(12) United States Patent
Mathias et al.

(10) Patent No.: US 7,479,131 B2
(45) Date of Patent: Jan. 20, 2009

(54) BIOLOGICAL FLUID SAMPLING APPARATUS, ASSEMBLY AND METHOD

(75) Inventors: Jean-Marie Mathias, Lillois (BE); Georges Rondeau, Braffe (BE); Michel Joie, Erange (BE)

(73) Assignee: Fenwal, Inc., Lake Zurich, IL (US)

( * ) Notice: Subject to any disclaimer, the term of this patent is extended or adjusted under 35 U.S.C. 154(b) by 464 days.

(21) Appl. No.: 10/279,252

(22) Filed: Oct. 24, 2002
(Under 37 CFR 1.47)

(65) Prior Publication Data
US 2004/0082899 A1 Apr. 29, 2004

Related U.S. Application Data

(63) Continuation-in-part of application No. 09/492,060, filed on Jan. 27, 2000, now Pat. No. 6,520,948, which is a continuation-in-part of application No. 09/364,628, filed on Jul. 29, 1999, now Pat. No. 6,387,086.

(60) Provisional application No. 60/364,314, filed on Mar. 14, 2002.

(51) Int. Cl.
*A61B 19/00* (2006.01)
(52) U.S. Cl. .................. 604/409; 604/408; 604/403
(58) Field of Classification Search ................ 604/403, 604/408, 409, 410, 411, 4.01–5.01, 6.15, 604/262; 600/575–580
See application file for complete search history.

(56) References Cited

U.S. PATENT DOCUMENTS

| | | |
|---|---|---|
| 2,868,201 A | 1/1959 | Gabriel |
| 2,950,716 A | 8/1960 | Bellamy et al. |
| 2,955,595 A | 10/1960 | Semple |
| 3,127,892 A | 4/1964 | Bellamy, Jr. et al. |
| 3,187,750 A | 6/1965 | Tenczar |
| 3,209,752 A | 10/1965 | Bujan et al. |
| 3,217,710 A | 11/1965 | Beall et al. |
| 3,342,179 A | 9/1967 | Ellmann |
| 3,395,696 A | 8/1968 | Brown |
| 3,416,528 A | 12/1968 | Kahn |
| 3,434,468 A | 3/1969 | Barr, Sr. et al. |
| 3,467,095 A | 9/1969 | Ross |
| 3,518,164 A | 6/1970 | Andelin et al. |

(Continued)

FOREIGN PATENT DOCUMENTS

DE 42 22 398 1/1994

(Continued)

OTHER PUBLICATIONS

Thomas Gibson & Walter Norris, "Skin Fragments Removed by Injection Needles," *The Lancet*, (1958), vol. 8, p. 983-985.

(Continued)

*Primary Examiner*—Leslie R Deak
(74) *Attorney, Agent, or Firm*—Cook Alex Ltd.

(57) ABSTRACT

A sampling apparatus is disclosed that includes a sample container including at least one wall defining a fluid-receiving interior chamber and including a fluid inlet for receiving fluid into the chamber and a sample device receiver carried by the container wall and in fluid communication with the chamber, the receiver being adapted to receive a sampling device for withdrawing a fluid sample from the chamber.

46 Claims, 13 Drawing Sheets

U.S. PATENT DOCUMENTS

| | | |
|---|---|---|
| 3,520,292 A | 7/1970 | Barr, Sr. et al. |
| 3,538,915 A | 11/1970 | Frampton et al. |
| 3,570,484 A | 3/1971 | Steer |
| 3,654,924 A | 4/1972 | Wilson et al. |
| 3,687,296 A | 8/1972 | Spinosa et al. |
| 3,741,217 A | 6/1973 | Ciarico |
| 3,788,369 A | 1/1974 | Killinger |
| 3,851,790 A | 12/1974 | Kasper |
| 3,945,380 A | 3/1976 | Dabney et al. |
| 3,955,423 A | 5/1976 | Ohringer |
| 3,965,889 A | 6/1976 | Sachs |
| 3,986,507 A | 10/1976 | Watt |
| 3,996,923 A | 12/1976 | Guerra |
| 4,056,101 A | 11/1977 | Geissler et al. |
| 4,063,460 A | 12/1977 | Svensson |
| 4,086,060 A | 4/1978 | Hermann, Jr. |
| 4,119,125 A | 10/1978 | Elkins |
| 4,120,662 A | 10/1978 | Fosslien |
| 4,152,269 A | 5/1979 | Babson |
| 4,207,870 A | 6/1980 | Eldridge |
| 4,266,543 A | 5/1981 | Blum |
| 4,278,437 A | 7/1981 | Haggar |
| 4,311,484 A | 1/1982 | Fosslien |
| 4,341,212 A | 7/1982 | Medwid |
| 4,346,052 A | 8/1982 | Knox |
| 4,392,499 A | 7/1983 | Towse |
| 4,407,660 A | 10/1983 | Nevens et al. |
| 4,409,990 A | 10/1983 | Mileikowsky |
| 4,432,755 A * | 2/1984 | Pearson .................. 141/329 |
| 4,444,203 A | 4/1984 | Engelman |
| 4,449,539 A | 5/1984 | Sarstedt |
| 4,465,200 A | 8/1984 | Percarpio |
| 4,507,123 A | 3/1985 | Yoshida |
| 4,509,534 A | 4/1985 | Tassin, Jr. |
| 4,511,359 A | 4/1985 | Vaillancourt |
| 4,516,977 A | 5/1985 | Herbert |
| 4,537,593 A | 8/1985 | Alchas |
| 4,560,382 A | 12/1985 | Isono |
| 4,620,549 A | 11/1986 | Nugent |
| 4,645,486 A | 2/1987 | Beal et al. |
| 4,655,764 A | 4/1987 | Sato |
| 4,670,013 A | 6/1987 | Barnes et al. |
| 4,687,474 A | 8/1987 | Takanashi |
| 4,691,580 A | 9/1987 | Fosslien |
| 4,717,386 A | 1/1988 | Simmons |
| 4,742,910 A | 5/1988 | Staebler |
| 4,756,201 A | 7/1988 | Uffenheimer |
| D298,567 S | 11/1988 | Morris |
| 4,782,841 A | 11/1988 | Lopez |
| 4,784,650 A | 11/1988 | Coburn |
| 4,786,286 A | 11/1988 | Cerny et al. |
| 4,791,938 A | 12/1988 | Van Valkenburg |
| 4,799,393 A | 1/1989 | Uffenheimer |
| 4,804,363 A | 2/1989 | Valeri |
| 4,813,940 A | 3/1989 | Parry |
| 4,820,297 A | 4/1989 | Kaufman et al. |
| 4,838,855 A | 6/1989 | Lynn |
| 4,838,871 A | 6/1989 | Luther |
| 4,840,618 A | 6/1989 | Marvel |
| 4,846,795 A | 7/1989 | Minagawa |
| 4,850,374 A | 7/1989 | Diaz-Ramos |
| 4,883,461 A | 11/1989 | Sawyer |
| 4,892,537 A | 1/1990 | Carmen et al. |
| 4,900,321 A | 2/1990 | Kaufman et al. |
| 4,900,322 A | 2/1990 | Adams |
| 4,911,694 A | 3/1990 | Dolan |
| 4,911,696 A | 3/1990 | Miyasaka et al. |
| 4,911,706 A | 3/1990 | Levitt |
| 4,917,867 A | 4/1990 | Jensen et al. |
| 4,932,418 A | 6/1990 | Coburn |
| 4,935,012 A | 6/1990 | Magre et al. |
| 4,941,883 A | 7/1990 | Venturini |
| 4,944,924 A | 7/1990 | Mawhirt et al. |
| 4,976,708 A | 12/1990 | Oshiyama |
| 4,994,039 A | 2/1991 | Mattson |
| 5,002,066 A | 3/1991 | Simpson et al. |
| 5,030,209 A | 7/1991 | Wanderer et al. |
| 5,045,067 A | 9/1991 | Ohnaka et al. |
| 5,046,509 A | 9/1991 | Kater |
| 5,061,365 A | 10/1991 | Utterberg |
| 5,086,780 A | 2/1992 | Schmitt |
| 5,098,371 A | 3/1992 | Juji et al. |
| RE33,924 E | 5/1992 | Valeri |
| 5,112,311 A | 5/1992 | Utterberg et al. |
| 5,122,129 A | 6/1992 | Olson et al. |
| 5,125,414 A | 6/1992 | Dysarz |
| 5,135,489 A | 8/1992 | Jepson et al. |
| 5,141,490 A | 8/1992 | Fujii et al. |
| 5,180,504 A | 1/1993 | Johnson et al. |
| 5,207,638 A | 5/1993 | Choski et al. |
| 5,259,843 A | 11/1993 | Watanabe et al. |
| 5,269,946 A | 12/1993 | Goldhaber et al. |
| 5,300,060 A | 4/1994 | Nelson |
| 5,330,462 A | 7/1994 | Nakamura |
| 5,352,191 A | 10/1994 | Sunago et al. |
| 5,358,482 A | 10/1994 | Panzani |
| 5,403,304 A | 4/1995 | Ishida |
| 5,417,681 A | 5/1995 | Miyake |
| 5,454,806 A | 10/1995 | Shinonome |
| 5,480,378 A | 1/1996 | Weis-Fogh et al. |
| 5,495,855 A | 3/1996 | Dudar et al. |
| 5,496,301 A * | 3/1996 | Hlavinka et al. ............ 604/409 |
| 5,512,187 A | 4/1996 | Buchholz et al. |
| 5,523,004 A | 6/1996 | Tanokura et al. |
| 5,527,472 A | 6/1996 | Bellotti et al. |
| 5,573,526 A | 11/1996 | Hess |
| 5,573,527 A * | 11/1996 | Macabasco et al. ......... 604/410 |
| 5,649,907 A | 7/1997 | Mori et al. |
| 5,702,383 A | 12/1997 | Giesler et al. |
| RE35,804 E | 5/1998 | Stewart |
| 5,752,936 A | 5/1998 | Chen |
| 5,755,673 A | 5/1998 | Kinsey |
| 5,769,826 A | 6/1998 | Johnson et al. |
| 5,769,839 A | 6/1998 | Carmen et al. |
| 5,772,608 A | 6/1998 | Dhas |
| 5,810,775 A | 9/1998 | Shaw |
| 5,820,582 A * | 10/1998 | Keilman ..................... 604/500 |
| 5,836,933 A | 11/1998 | Buttitta et al. |
| 5,858,015 A | 1/1999 | Fini |
| 5,879,318 A | 3/1999 | Van Der Heiden et al. |
| 5,928,214 A | 7/1999 | Rubinstein et al. |
| 5,984,912 A | 11/1999 | Niedospial, Jr. et al. |
| 6,106,502 A | 8/2000 | Richmond |
| 6,113,555 A | 9/2000 | Parmigiani |
| 6,123,859 A | 9/2000 | Lee et al. |
| 6,132,413 A | 10/2000 | Mathias et al. |
| 6,152,901 A | 11/2000 | Arruego et al. |
| 6,193,675 B1 | 2/2001 | Kraus et al. |
| 6,234,538 B1 | 5/2001 | Lauer |
| 6,241,717 B1 | 6/2001 | Niedospial, Jr. |
| 6,267,564 B1 | 7/2001 | Rapheal |
| 6,280,401 B1 | 8/2001 | Mahurkar |
| 6,287,265 B1 | 9/2001 | Gleason |
| 6,306,118 B1 | 10/2001 | Crawford et al. |
| 6,325,775 B1 | 12/2001 | Thom et al. |
| 6,328,726 B1 | 12/2001 | Ishida et al. |
| 6,344,139 B1 | 2/2002 | Utterberg |
| 6,358,420 B2 | 3/2002 | Blickhan et al. |
| 6,364,847 B1 | 4/2002 | Shulze et al. |
| 6,387,069 B1 | 5/2002 | Utterberg |
| 6,387,086 B2 * | 5/2002 | Mathias et al. .............. 604/409 |
| 6,394,993 B1 | 5/2002 | Chang et al. |
| 6,485,469 B1 | 11/2002 | Stewart et al. |
| 6,491,679 B1 | 12/2002 | Okamoto et al. |

| | | | |
|---|---|---|---|
| 6,495,039 B1 | 12/2002 | Lee et al. | |
| 6,500,129 B1 | 12/2002 | Mahurkar | |
| 6,517,508 B1 | 2/2003 | Utterberg et al. | |
| 6,520,948 B1 * | 2/2003 | Mathias et al. | 604/409 |
| 6,540,696 B1 | 4/2003 | Dillon et al. | |
| 6,585,875 B1 | 7/2003 | Ryabkov | |
| 6,592,613 B1 | 7/2003 | Ishida et al. | |
| 6,626,884 B1 | 9/2003 | Dillon et al. | |
| 6,669,905 B1 | 12/2003 | Mathias et al. | |
| 6,692,479 B2 | 2/2004 | Kraus et al. | |
| 6,946,079 B1 | 9/2005 | Holm | |
| 2001/0025167 A1 | 9/2001 | Kraus et al. | |
| 2001/0052497 A1 | 12/2001 | Blickhan et al. | |
| 2002/0019621 A1 | 2/2002 | Mathias et al. | |
| 2002/0151834 A1 | 10/2002 | Utterberg | |
| 2002/0183679 A1 | 12/2002 | Deverre | |
| 2003/0144607 A1 | 7/2003 | Mathias et al. | |
| 2003/0176813 A1 | 9/2003 | Mathias et al. | |
| 2003/0208151 A1 | 11/2003 | Kraus et al. | |
| 2004/0015147 A1 | 1/2004 | Mathias et al. | |
| 2004/0019344 A1 | 1/2004 | Peterson et al. | |
| 2004/0082898 A1 | 4/2004 | Mathias | |
| 2004/0106890 A1 | 6/2004 | Goudaliez et al. | |
| 2005/0143712 A1 | 6/2005 | Mathias | |
| 2005/0148993 A1 | 7/2005 | Mathias | |
| 2006/0111658 A1 | 5/2006 | Mathias | |
| 2006/0111687 A1 | 5/2006 | Mathias | |

FOREIGN PATENT DOCUMENTS

| | | |
|---|---|---|
| DE | 200 10825 U1 | 11/2000 |
| EP | 0 002 028 | 4/1981 |
| EP | 0 587 347 | 3/1994 |
| EP | 1 064 959 A1 | 1/2001 |
| EP | 1 190 673 | 3/2002 |
| FR | 1 586 087 | 2/1970 |
| JP | 10211274 A | 8/1998 |
| WO | WO 87/06813 | 11/1987 |
| WO | WO 98/28057 | 7/1998 |
| WO | WO 00/07642 | 2/2000 |

OTHER PUBLICATIONS

Morris Blajchman et al., "Bacteria in the Blood Supply: An Overlooked Issue in Transfusion Medicine," *Blood Safety and Current Challenges*, (1992), p. 213-228.

B.B. Barrett et al., "Strategies for the Avoidance of Bacterial Contamination of Blood Components," *Transfusion*, (1993), vol. 33, No. 3, p. 228-233.

P.I. Figueroa et al., "Distribution of Bacteria in Fluid Passing Through an Inoculated Collection Needle," *Transfusion Medicine*, (1995), vol. 35, suppl. 10, p. 11s, Abstract # S42.

A.M. Soeterboek et al., "Prevalence of Bacterial Contamination in Whole-Blood after Donation," *Vox Sanguinis*, (1995), vol. 69, p. 149.

H. Olthuis et al., "A Simple Method to Remove Contaminating Bacteria During Venepuncture," *Vox Sanguinis*,(1996), vol. 70, suppl. 2, p. 113, Abstract # 1/2C-33 OP; Karger Medical and Scientific Publishers, Makuhari Messe, Japan.

C. Vassort-Bruneau, P. Perez et al., "New Collection System to Prevent Contamination with Skin Bacteria," *Transfusion Medicine: 25th Congress of International Society of Blood Transfusion*,(1996), vol. 74, suppl. 1, Abstract 1039; Karger Medical and Scientific Publishers, Oslo, Norway.

Claes Högman, "Serious Bacterial Complications from Blood Components—How Do They Occur?," *Transfusion Medicine*, (1998), vol. 8, p. 1-3.

C. Vassort, P. Allouch et al., "Efficacy of a Collection Procedure on Bacterial Contamination During Venous Puncture," *Transfus Clin Biol*, (1998), vol. 5, suppl. 1, Abstract 06-6.

Dirk de Korte et al., "Determination of the Degree of Bacterial Contamination of Whole-Blood Collections Using an Automated Microbe-Detection System," *Transfusion*, (2000), vol. 41, p. 815-818.

S.J. Wagner, D. Robinette, L.I. Friedman, & J. Miripol, "Diversion of Initial Blood Flow to prevent Whole-Blood Contamination By Skin Surface Bacteria: An In Vitro Model," *Transfusion*, (2000), vol. 40, p. 335-338.

M. Chassaigne, C. Vassort-Bruneau, P. Allouch, A. Audurier et al., "Reduction of Bacterial Load by Predonation Sampling," *Transfusion and Apheresis Science*, (2001), vol. 24, p. 253.

P. Perez et al., "Multivariate Analysis of Determinants of Bacterial Contamination of Whole-Blood Donations," *Vox Sanguinis*, (2001), vol. 82, p. 55-60.

Dirk de Korte et al. "Diversion of First Blood Volume Results in a Reduction of Bacterial Contamination for Whole-Blood Collections," *Vox Sanguinis*, (2002), vol. 83, p. 13-16.

Roger Dodd, "Bacterial Contamination of Blood Components," *American Red Cross*.

Haemonetics, *Introducing the MCS3P Multi-component System*, (1993). [Brochure].

Baxter, *Fenwal®: Access Closed System Apheresis Kit for Single Venous Access*, (1994).

Foi, *FDA 501(k) Filing for COBE Spectra Extended Life Platelet Set with Integrated Leukoreduction Filter*, (1995).

Baxter, Brochure for Amicus® Separator—Single Needle Draw (1996).

C. Rose et al., "Evaluation [of] the MCS® + LN 9000 Continuous (In-Line) Leukoreduction Filter;" *Haemonetics Blood Services & Training Institute*, Tucson, Arizona.

Haemonetics, "Timing is Everything: Leukoreduction Your Platelets Before Storage." [Brochure].

U.S. Appl. No. 09/442,210, filed Nov. 17, 1999, Mathias et al.

"Procedure d'utilisation de la poche de prelevement a sang total avec Protecteur D'Aiguille," in French with English translation, published by Baxter International Inc., Biotech Group, Jun. 1997.

"Optipac Blood Pack System with Sampling Holder and Bloodpack Needle Protector (BNP)," Baxter International Inc., Fenwal Division, Jan. 13, 1998.

* cited by examiner

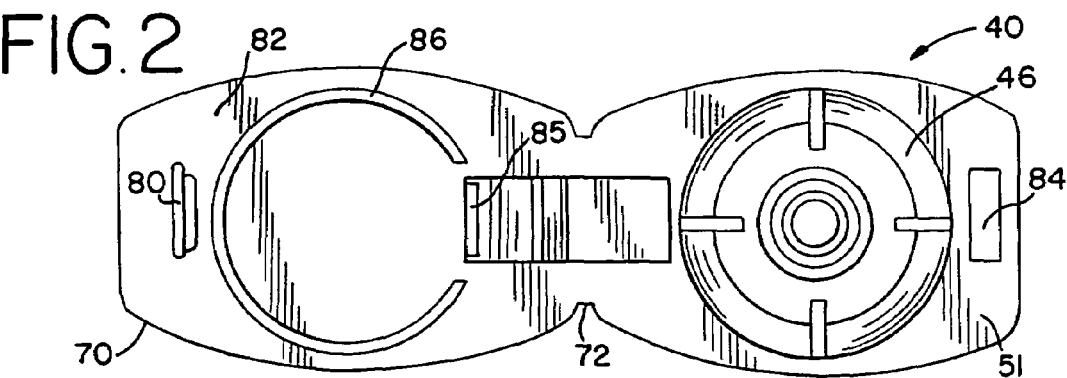
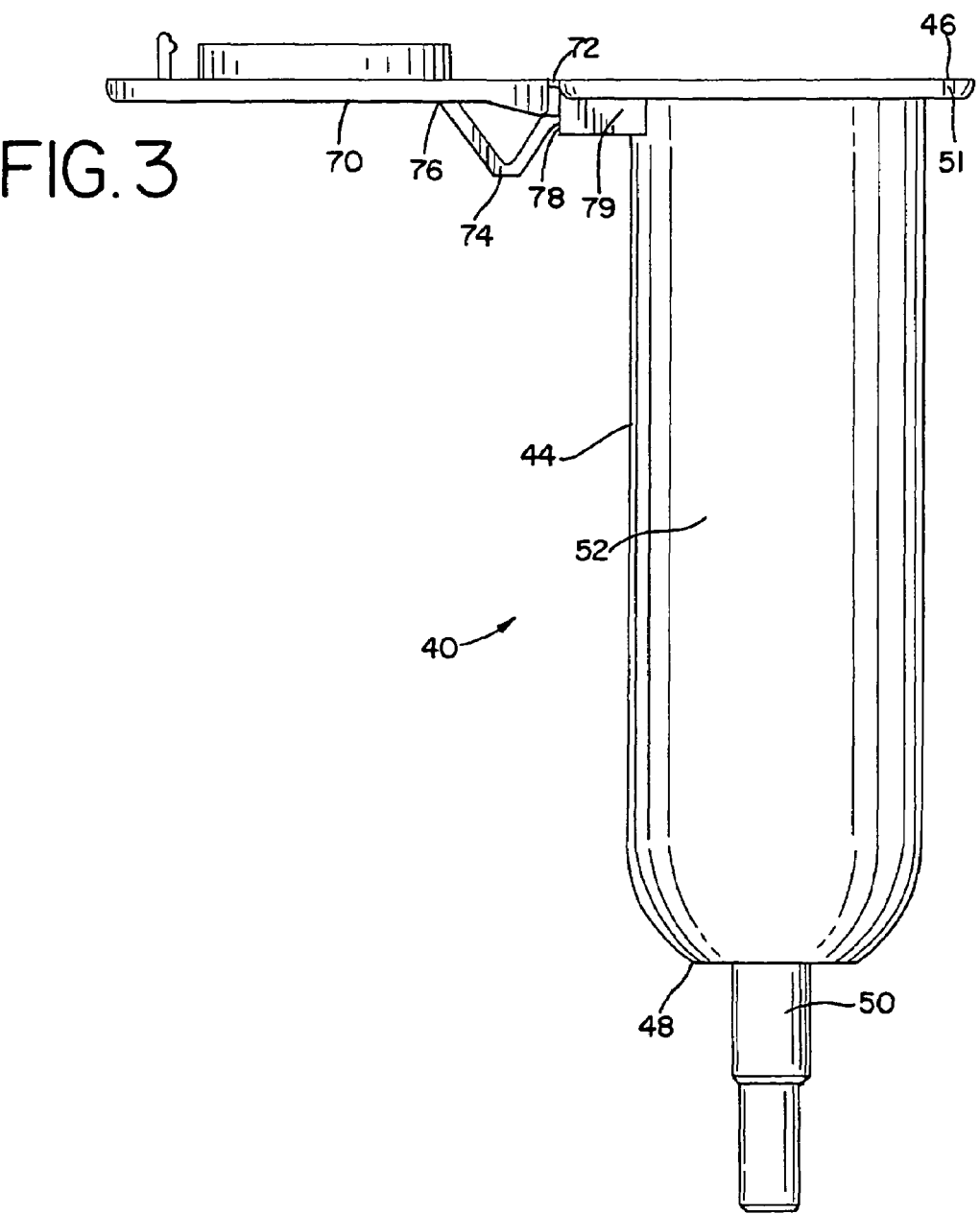

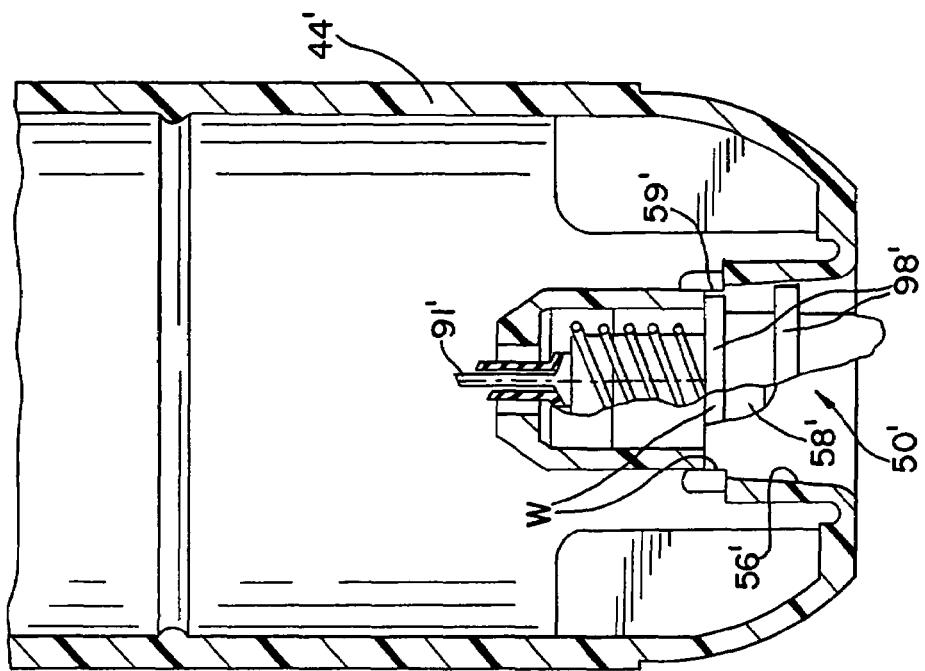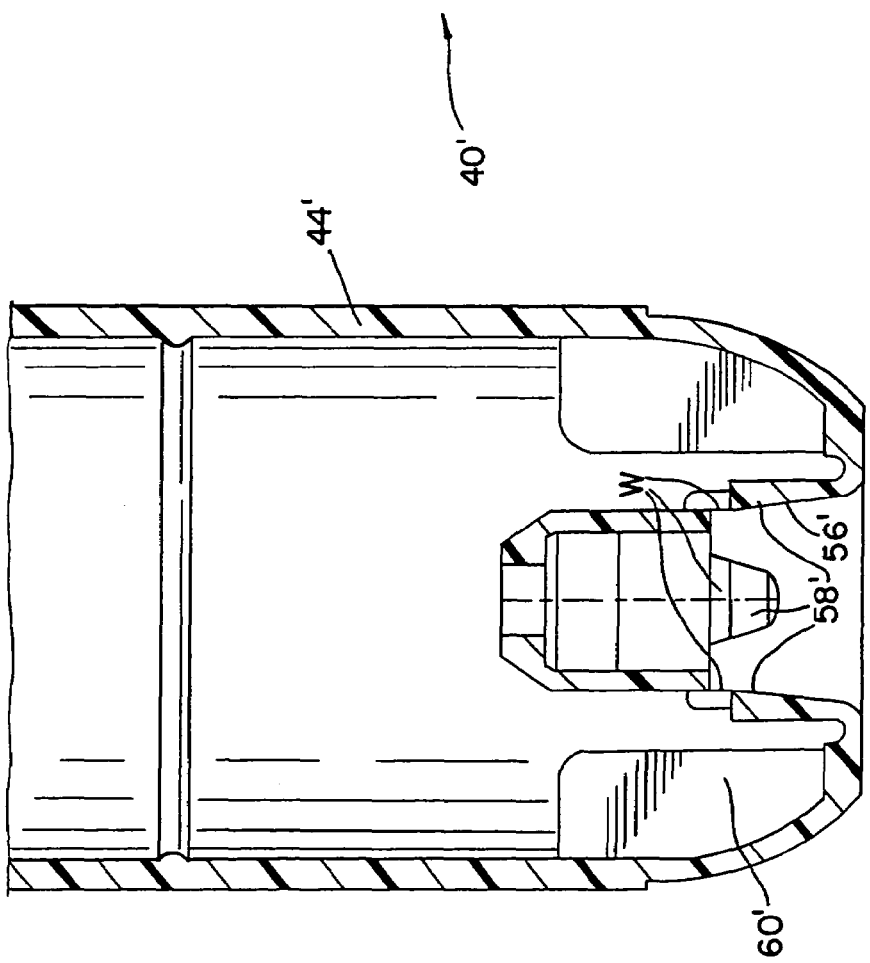

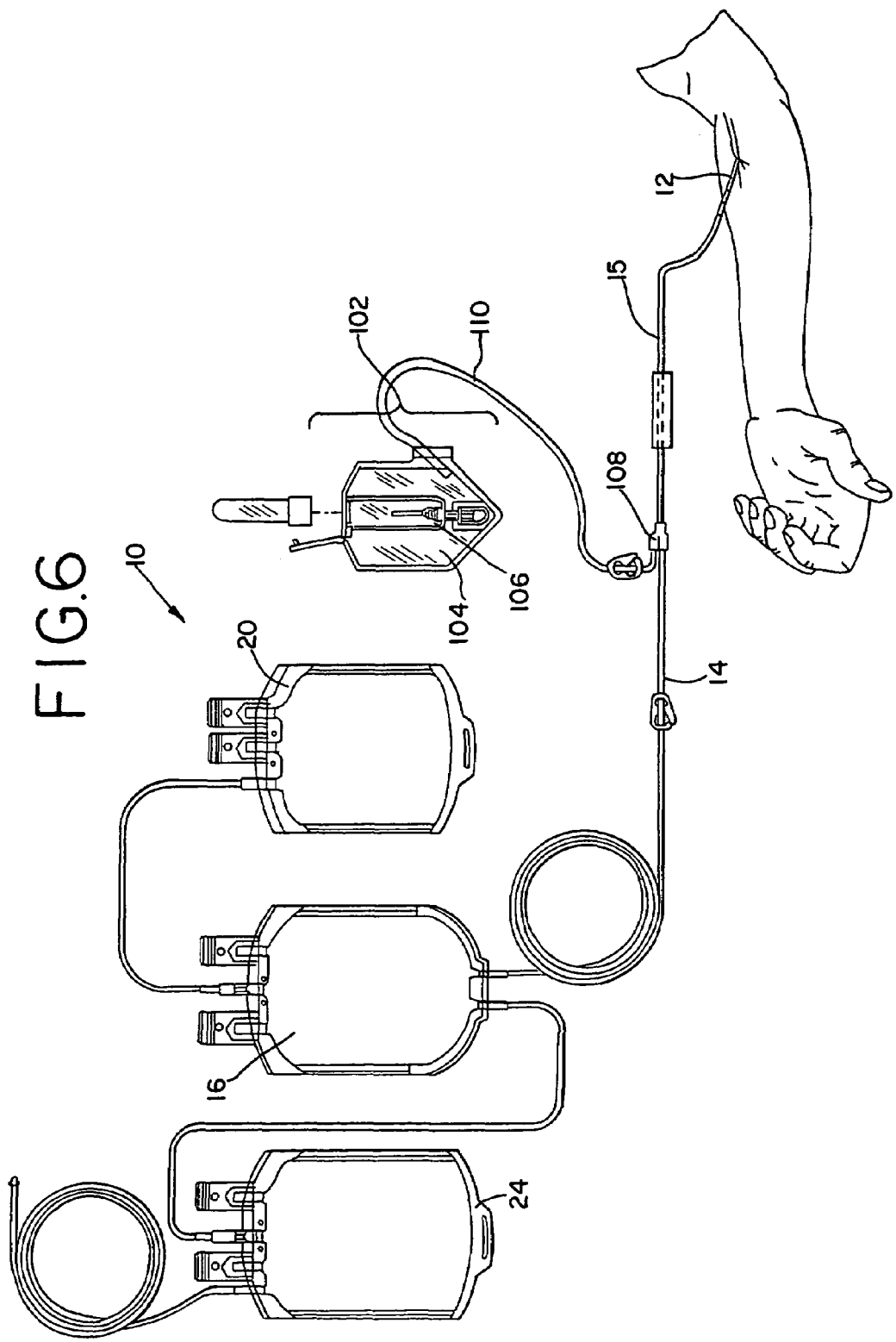

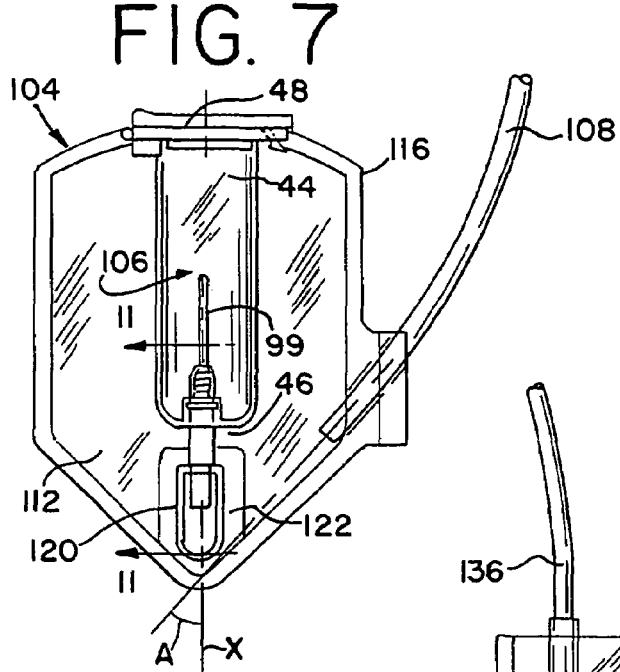
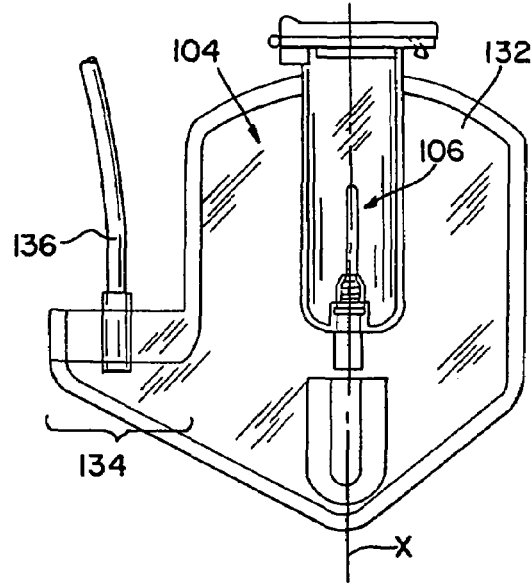
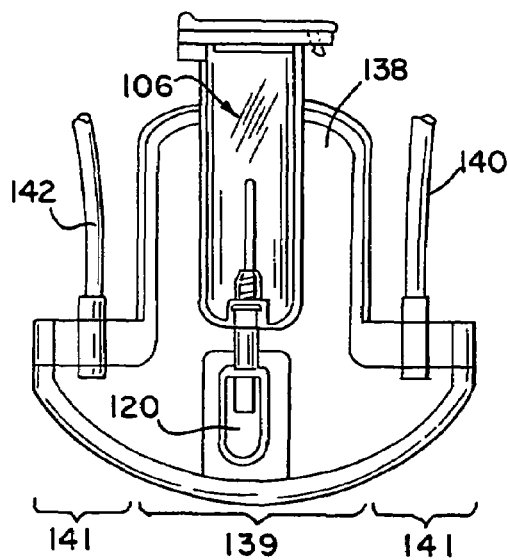
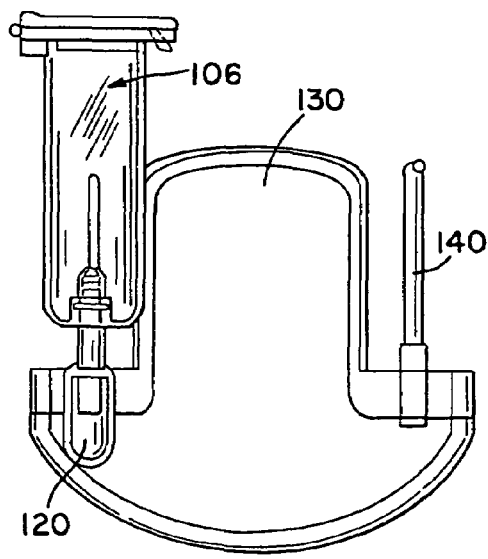

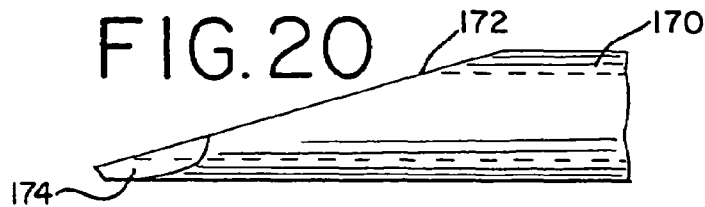
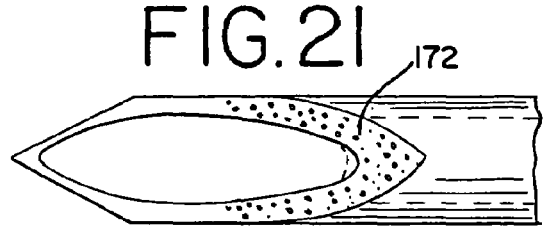
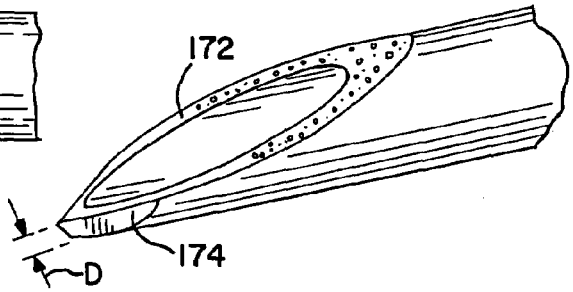
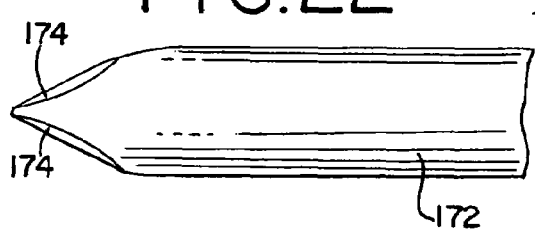
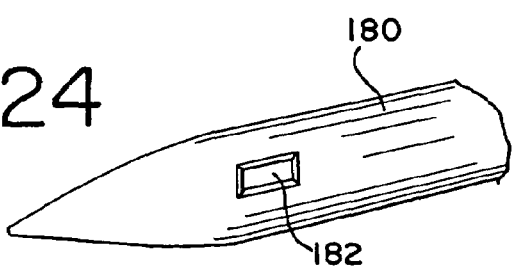
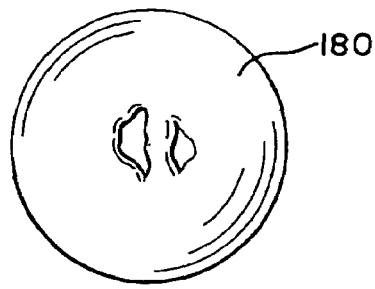
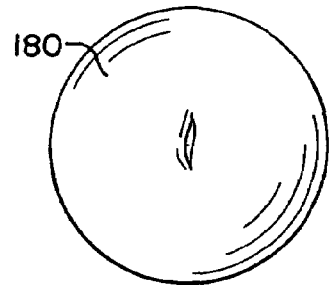

BIOLOGICAL FLUID SAMPLING APPARATUS, ASSEMBLY AND METHOD

This application claims the benefit of U.S. Provisional Patent Application Ser. No. 60/364,314, filed Mar. 14, 2002, and is also a continuation-in-part of U.S. application Ser. No. 09/492,060, filed Jan. 27, 2000 now U.S. Pat. No. 6,520,948, which is a continuation-in-part of U.S. application Ser. No. 09/364,628, filed Jul. 29, 1999 now U.S. Pat. No. 6,387,086, and incorporates by reference each of the above-identified applications.

The present invention relates to sampling apparatus suitable for collecting or taking samples of biological fluid, such as blood or blood components, from fluid circuit assemblies employed in the collection, separation, storage or processing of biological fluids.

BACKGROUND OF THE INVENTION

Disposable fluid circuit assemblies are typically used for collecting, storing, separating and/or other processing of biological fluids, such as blood from a donor, patient or other source. They are commonly preassembled, presterilized and fully disposable for safety and convenience. These assemblies may include plastic tubing, containers, valves, flow control modules and the like for controlling fluid flow through the assembly. When employed on the collection or processing of blood and blood components, these assemblies typically include a venipuncture needle for insertion into the arm of a donor or patient. The needle is usually attached to one end of a flexible plastic tube which provides a flow path for the blood to the rest of the fluid circuit assembly. The other end of the plastic tube may be attached, either directly or indirectly, to one or more plastic bags or containers for collecting the withdrawn blood or a component of blood, such as concentrated red cells or platelets, or plasma. Such fluid circuit assemblies may be employed in manual blood collection procedures, where whole blood is collected from a donor for later off-site processing, or in automated procedures, where the fluid circuit is mounted on a reusable device, such as a centrifuge or other separator, that automatically controls flow of blood or components through the assembly. When used for blood collection, these fluid circuit assemblies are commonly called blood sets or apheresis sets.

The fluid circuit assembly may also include a sampling sub-unit to provide for collection of a sample of blood or blood component, which can be used for testing. It is known to use pierceable junctions in the fluid circuit to allow the user to extract a sample at the desired location. This has associated with it, however, a risk of accidental needle puncture as well as undesirable pooling of the fluid at the location of the sample port.

As shown in U.S. Pat. No. 5,496,301, it is also known to use a sample bag or pouch that is connected by a length of tubing to a sample tube holder for cooperating with vacuum sample tube, such as the Vacutainer™ sample collection tube marketed by Becton-Dickinson Co. of Franklin Lake, N.J. The holder includes a cylindrical shield and an internal needle within an elastomeric sheath for cooperation with the Vacutainer™ tube.

The arrangement illustrated in the above patent, however, is not as conductive to ease of manufacture or economy of packaging as may be desired. Also, in addition to other apparent shortcomings, it requires manual manipulation, such as inversion and the like to retrieve a sample and may not allow for easy and rapid withdrawal of the entire sample contained in the sample bag.

SUMMARY OF THE INVENTION

The present invention, is embodied, in one aspect, in a combination sampling container and a sample device receiver are provided. In accordance with this aspect of the present invention, the sample container includes at least one wall defining an interior fluid chamber and a fluid inlet for receiving fluid into the chamber. The sample device receiver in this combination is carried by the container wall and is in fluid communication with the chamber to permit withdrawal of samples therefrom.

In accordance with a further aspect, the present invention is embodied in a flexible sample container itself. In this regard, the flexible container of the invention includes an interior chamber defined by a pair of flexible facing plastic sheets that are peripherally sealed together, and an inlet tube is attached to the container in communication with the chamber. The container is adapted for hold in a selected, preferably vertical position and has an imaginary vertical axis when in that position. The inlet tube extends through the peripheral edge of the container at an acute angle to the vertical axis to compliment holding the container in a vertical disposition.

In yet another aspect of the present invention, the sample container is a pouch comprising a pair of flexible facing sheets peripherally sealed together along a peripheral edge to define an interior chamber and is adapted for holding in a vertical disposition. A blood component inlet tube communicates with the chamber, and the peripheral edge is inclined to direct fluid in the chamber to a lowermost region of the chamber, and a fluid sample exit opening is located in one of the sheets in the lowermost region.

The various aspects of the present invention may have stand-alone application, but also are of particular use as part of a biological fluid circuit assembly used for processing, storing, treating or separating a biological fluid in general and blood or blood components in particular. In accordance with this aspect, the present invention is generally embodied in a disposable closed fluid circuit assembly which includes an inlet for receiving a biological fluid into the fluid circuit assembly, and one or more flow paths for conducting the biological fluid or components thereof between selected locations within the fluid circuit. A sample container or pouch as summarized above, either alone or in combination with a sample device receiver, may be used in combination with the fluid circuit assembly to enhance product manufacturing and/or packaging, sample collecting and/or taking, and/or user safety.

In yet another aspect, a method for taking a sample of biological fluid is disclosed. The method includes providing a sampling apparatus. The sampling apparatus includes a sample container including at least one wall defining a fluid-receiving interior chamber and a fluid inlet for receiving fluid into the chamber. The sampling apparatus also includes a sample device receiver carried by the container wall is in fluid communication with the chamber, the receiver being adapted to receive a sampling device for withdrawing a fluid sample from the chamber wherein the sample receiver further comprises a tubular member with a proximal end and a distal end and a cover removably covering the proximal end and wherein the method includes opening the cover. The method further includes holding the sample device receiver and sample containers such that the receiver is disposed to receive the sample device into operative position for sample withdrawal in a generally vertical direction. The sample device is inserted into the receiver in a generally vertically downward direction, the sample receiver communicating with a lowermost region of the sample container as held so as to withdraw a sample generally vertically into the sample device. The method further comprises withdrawing the sample device after a sample is withdrawn and closing the cover over the proximal end.

BRIEF DESCRIPTION OF DRAWINGS

FIG. 2 is a top view of the receiver or holder assembly of FIG. 1 with the cover in an open position.

FIG. 3 is a side view of the receiver assembly of FIG. 2 with the cover in an open position.

FIG. 5A is a side cross-sectional view of a sample tube receiver in the present invention, without the needle assembly.

FIG. 5B is a side cross-sectional view of the sample tube receiver of FIG. 5A with a needle assembly, partially removed, in place.

FIG. 6 is a plan view of a manual fluid circuit assembly embodying sampling apparatus of the present invention.

FIG. 7 is a plan view of sampling apparatus of the present invention shown in FIG. 6, including a container and a sample tube receiver.

FIG. 8 is a plan view of an alternative embodiment of sampling apparatus of the present invention.

FIG. 9 is a plan view of a further alternative sampling apparatus of the present invention.

FIG. 10 is a plan view of a still further alternative sampling apparatus of the present invention.

FIG. 20 is a side view of a piercing needle particularly useful in the sampling apparatus of the present invention.

FIG. 21 is a top view of the needle of FIG. 20.

FIG. 22 is a bottom view of the needle of FIG. 20.

FIG. 23 is perspective view of the needle of FIG. 20.

FIG. 24 is a perspective view of another needle that may have application in the sampling apparatus of the present invention.

FIG. 25 illustrates the surface of a pierceable septum after repeated piercing by a prior art needle.

FIG. 26 illustrates the surface of a pierceable septum after repeated piercing by the needle of FIGS. 20-23.

DETAILED DESCRIPTION OF THE DRAWINGS

Figure 14:
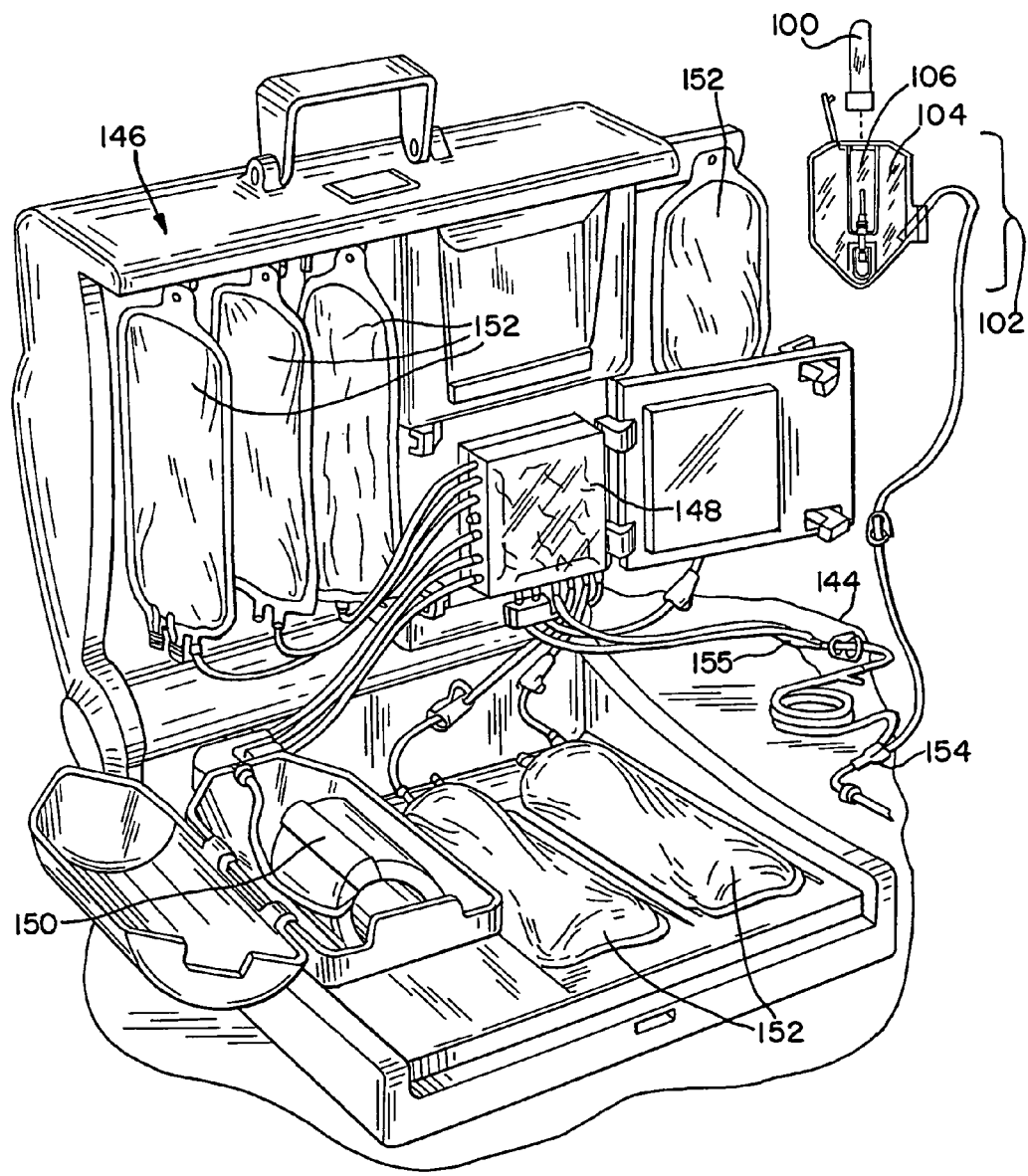
FIG. 14 is a perspective view of a fluid circuit assembly mounted on a reusable device for automated blood processing, and embodying the present invention.

Turning first to FIGS. 1-5, there is shown, among other things, a holder or receiver (holder and receiver are used interchangeably herein) assembly 40 employed in the present invention. The holder assembly 40 may be part of a presterilized fluid circuit assembly such as a blood collector and processing set 10 for the manual collection of blood from a donor 11, shown in FIG. 1. Alternatively, holder assembly 40 may be part of an apheresis processing set for the automated collection of blood and blood components as illustrated in FIG. 14.

It will also be appreciated that the holder assembly of the present invention may be provided as a "stand-alone" device (i.e., not used with a processing set of the type shown or described above) for "direct" withdrawal of blood from a donor or patient. An example of what is meant by a "stand-alone" device is described in U.S. Pat. No. 5,372,143, which is incorporated herein by reference. Another embodiment of a "stand-alone" receiver of the present invention includes a "double-needled" holder assembly where one of the needles is directly inserted into the vein of a donor or patient. For purposes of the following discussion, however, the holder or receiver assembly shall be described in conjunction with a sample collection container, which may be part of a larger fluid circuit assembly, such as the disposable blood collection and processing set of FIG. 1.

Figure 1:
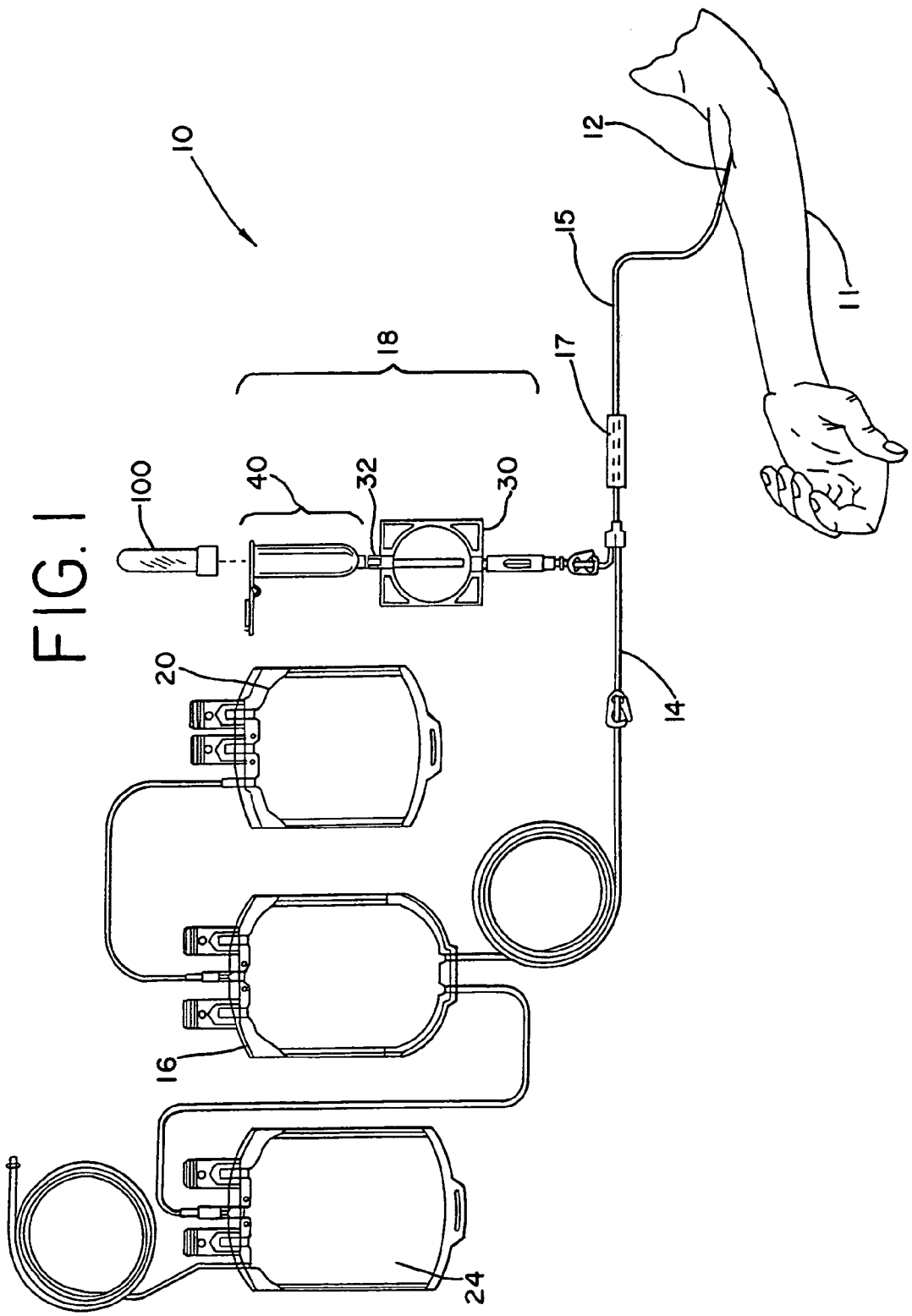
FIG. 1 is a plan view of a biological fluid circuit assembly in the form of disposable blood collection or processing set including a sampling apparatus employed in the present invention.

As shown in FIG. 1, the illustrated disposable blood collection/processing set 10 may include a needle such as venipuncture needle 12, and plastic tubings 14 and 15 extending from needle 12 to a collection container such as a flexible plastic container 16. A needle protector 17 may also be provided for retraction and storage of needle 12 after use.

The blood processing set 10 may include a single blood collection container 16 or, more preferably, as shown in FIG. 1, may include additional containers such as 20 and 24 for separation, storage or other processing of the collected blood or blood components. In accordance with one particular, non-limiting embodiment, the disposable processing set 10 may include a sampling sub-unit 18, including sampling container or pouch 30.

In a preferred embodiment, sampling sub-unit 18 includes a receiver or holder assembly 40 of the present invention. Receiver assembly 40 may be pre-attached to blood sampling tube 32 of sampling container or pouch 30, thereby establishing flow communication between the holder assembly and the pouch interior. Details of the blood collection and blood sampling procedures using the above-described sets are described in U.S. Pat. Nos. 6,387,086 and 6,520,948, incorporated by reference.

In one embodiment (shown in FIG. 3), receiver assembly 40 includes an elongated hollow cylindrical housing 44, although other shapes or geometries may also be employed. Housing 44 includes a proximal end 46 and distal end 48. Housing 44 is open (and/or openable) at its proximal end 46 and is adapted for receiving therethrough a blood collection tube 100, such as a Vacutainer™ vacuum collection container.

In a preferred embodiment (described in greater detail below), housing 44 of holder assembly 40 includes a cover 70 for closing the open proximal end 46 of the housing 44. The distal end 48 of the housing 44 is generally closed except for external access through a needle subassembly 50 (described in greater detail below with reference to FIG. 5) secured to the housing 44 at the distal end 48.

Housing 44 may be made of any suitable, plastic material that can be injection molded and sterilized by known forms of sterilization, such as autoclaving (steam sterilization) or radiation. A preferred, autoclavable plastic material is polypropylene. Where holder assembly 40 is sterilized by electron beam or gamma radiation, suitable materials may include polystyrene. Of course, still other materials known to those of skill in the art may also be used.

As shown in FIG. 3, in one embodiment, cylindrical housing 44 may optionally include flange 51 at or near the open proximal end 44. Sidewall 52 of housing 44 extends from flange 51 to distal end 48. At the distal end 48, as seen in FIG. 5, side wall 52 is interrupted by axial through bore 54, centered within the distal end, and adapted to receive needle subassembly 50.

Figure 5:
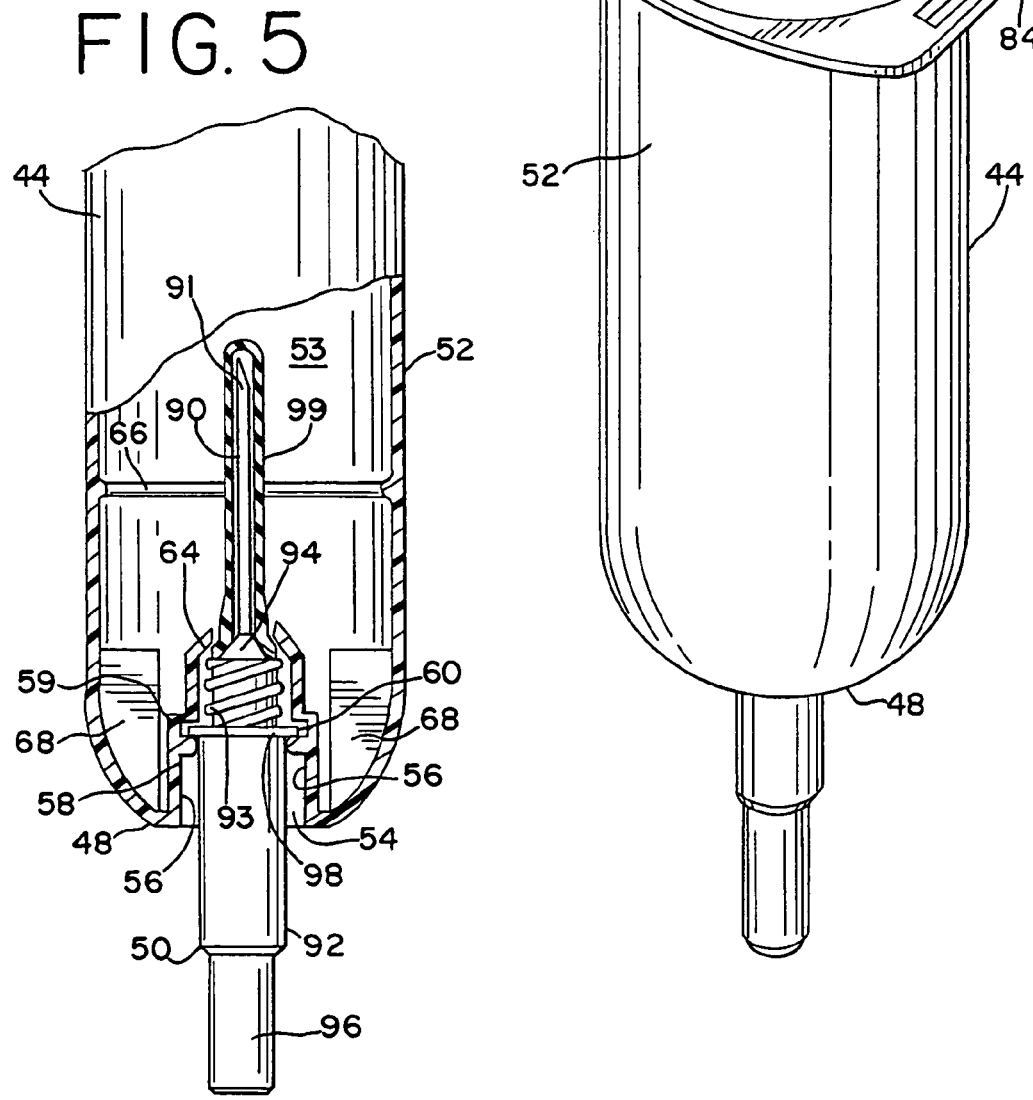
FIG. 5 is a partial side view of the receiver assembly with a portion of the outer sidewall broken away to show the holder assembly interior in cross-section.

As best seen in FIG. 5, axial bore 54 is defined by an interior wall 56. The housing 44 and needle subassembly 50 preferably have interlocking surfaces for fixedly holding the needle assembly in the through bore. The interlocking surfaces may be of a variety of different arrangements. As seen in FIG. 5, wall 56 may include an interior annular shoulder or ledge 59 and a radially inwardly extending rib 58 located proximally from the distal end 48. The inwardly extending ledges or ribs 58 and 59 are spaced apart from each other to provide an annular slot 60 in the interior wall 56.

As further shown in FIG. 5, the diameter of distal axial bore 54 is smaller in the area proximal to second inwardly extending ledge 59, than in the area distal to the first inwardly extending ledge 58. In the illustrated embodiment, the diameter of axial bore 54 is further narrowed by inwardly radially inclined wall portion 64.

As shown in FIG. 5, housing 44 may also include an inner, radially inward collar or ring 66. Collar 66 may be provided as a ledge or projection extending from the interior surface of sidewall 52 into the housing interior 53. Collar 66 provides a means for frictionally retaining the needle protector 17 (with a used venipuncture needle retracted therein), which may be inserted into housing 44 after blood collection procedure is completed, as generally described in U.S. Pat. No. 6,632,201, which is incorporated herein by reference. Housing 44 may also include a stop surface for engaging the end of a blood sampling tube 100. In the illustrated embodiment stop surfaces are provided by the proximal ends of ribs 68 in the distal end of the housing interior 53.

Housing 44 of needle holder assembly 40 preferably includes a cover, such as cap 70 for opening and closing proximal end 46 of the cylindrical housing. Cap 70 may be separately provided or, more preferably, may be attached to housing 44, as shown in the figures. In one embodiment (see FIGS. 3 and 4), cap may be a "flip cap" attached to the flange 51 by hinge 72. Hinge 72 may be formed by reducing (during the injection molding process) the amount of plastic material and, thus, the thickness in the section between cap 70 and flange 51, allowing for easy bending along the hinge.

Figure 3A:
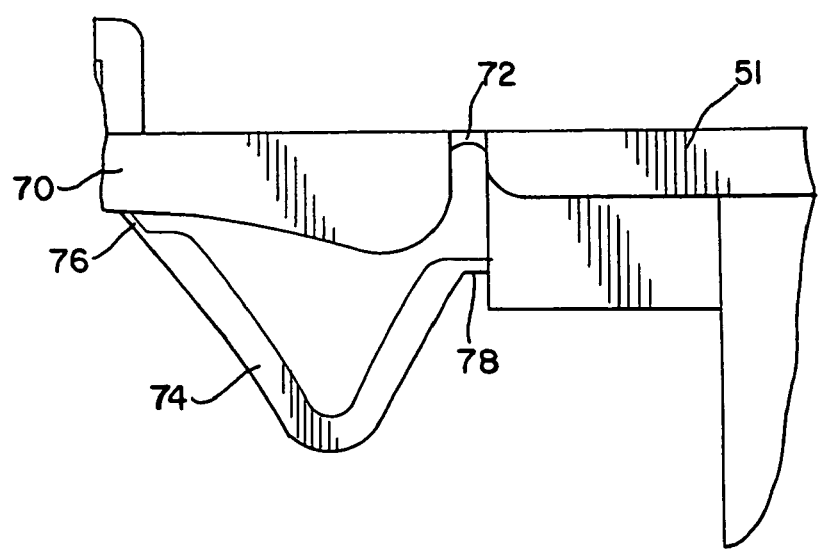
FIG. 3A is an enlarged side view of the hinge arrangement of the receiver in FIGS. 2 and 2A.
Figure 4:
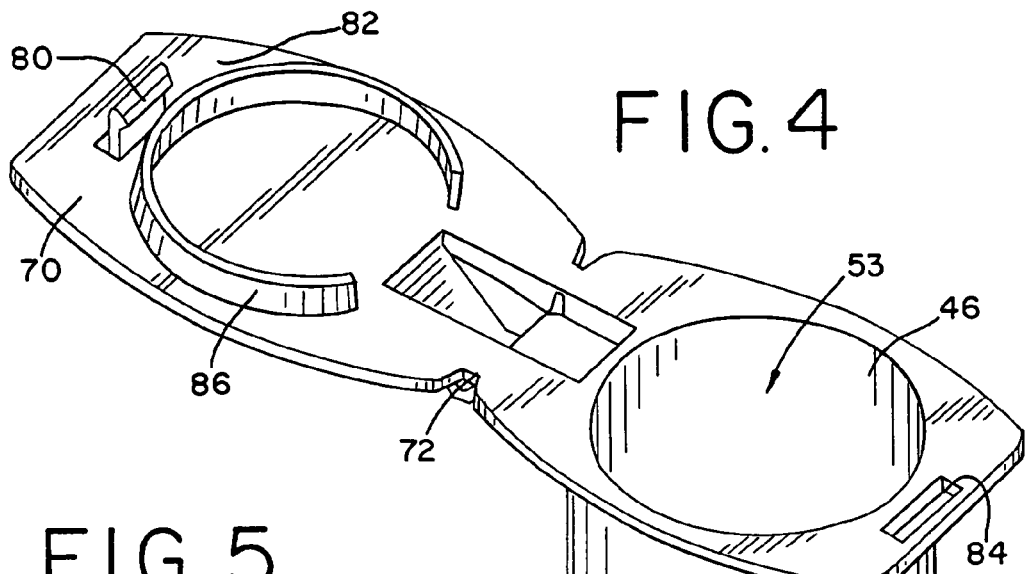
FIG. 4 is a perspective view of the receiver assembly of FIG. 2 with the cover in the open position.

As shown in FIGS. 3 and 3A, cap 70 may also be provided with spring type or plastic "living hinge" closure member 74. One end of closure member 74 is attached to the cap 70 along thin web 76 while the other end 78 of closure member 74 is attached to base 79 of flange 51 along thin web 78. Closure member 74 biases the cap to either an open position or a closed position preferentially to an intermediate position, so as to allow for "one handed" and, in fact, "one-fingered" opening and closing of cap 70. With a single flick of the thumb or finger, the technician can open or close the cap as necessary. Closure member 74 causes cap 70 to either snap open or snap closed, and tends to move the cap away from an intermediate position to the open or closed position preferentially to an intermediate position. In other embodiments, cap 70 may be provided as a tethered cap (i.e., tethered to housing 44), a cap that slides over the open proximal end, a cap that rotates between an open and closed position, or other arrangement. A peel off seal or cover, sealed adhesively or otherwise bonded to the open end of housing 44 could also be used to provide a sterile barrier over the open end of housing 44 until a sample is required.

As further shown in FIGS. 2 and 3, cap 70 may include a latch 80 on the inner surface 82 of cap 70. When cap 70 is in the closed position, latch 80 is received within slot 84 of flange 50. Cap 70 may also include centering ring 86 for centering cap 70 over open proximal end 46 and, thereby ensuring proper closure. Optional gap 85 between spring 74 and cap 70 allows for venting of housing interior 53 during, for example, steam sterilization.

Turning now to the needle subassembly 50, it will be appreciated that needle subassembly may be integrally joined to housing 44 as a one-piece arrangement or attached by adhesive or melt bonding or, more preferably, the needle subassembly may be separately formed and adapted for interference fit to housing 44 by interlocking surfaces. Needle subassembly 50 may include a proximal piercing end 90 and distal non-piercing end 92. Although referred to as a needle assembly, it is absolutely necessary that the member for a needle be used to pierce the septum of the sample tube. A blunt cannula or the like could also be used with those sample tubes that would accommodate such. Also, where holder assembly is a "stand-alone" type assembly intended for direct use with a donor or patient, needle assembly 40 may include a distally-pointed needle, for example, a double-ended needle where both the proximal and distal ends include piercing ends. Optionally, the proximal and/or distal ends of the piercing member could have the well-known blunt cannula configuration to provide greater safety against accidental needle sticks, as described above.

With reference to the embodiment shown in FIG. 5, first proximal piercing end 90 includes piercing member 91 attached to hub 94. Piercing member 91 may be a hollow needle or cannula made of stainless steel or other rigid metal or plastic. The opposite facing distal non-piercing end 92 preferably includes a luer 96 with an internal fluid path but a blunt cannula or needle could also be used if desired. The internal fluid path of the distal end is in fluid communication with the hollow interior of the proximal needle (piercing member) 91 via a through bore in the needle hub.

As an alternative to snap attachment, the portion 93 of the body of needle subassembly between luer 96 and hub 94 may, optionally, be threaded to allow attachment to housings having a threaded axial bore. However, in a preferred embodiment, needle subassembly 50 is not screwed into housing 44, but is instead press-fit into housing 44. In one press-fit arrangement, needle subassembly 50 may include an outwardly extending radial ring 98 for press fit engagement with housing 44. Specifically, as needle subassembly 50 is advanced into axial bore 54, ring 98 is captured within slot 60. Further movement in the proximal or distal directions is prevented by inwardly extending rib or ledge 58 and 59, thus providing a secure attachment of needle subassembly 50 to housing 44. These structures could be reversed, with the needle hub having a pair of spaced ribs defining a slot therebetween and the housing having an annular rib for snap fit into the slot. Other structures, such as detents, latches and the like, could also be used for snap fit assembly. A secure fit is partially desired so as to avoid blood leakage.

Needle 91 is preferably enclosed within a flexible, resilient protective sheath such as a rubber (latex) sleeve, or more preferably a polyisoprene or other non-latex sleeve 99. Sleeve 99 is located over needle 91 and hub 94. Hub 94 may include an outwardly extending ring (not shown), to provide a tight fit between hub 94 and the distal end of the sleeve, and thereby hold sleeve 99 in place. Other techniques may also be used for attaching the sleeve to the needle hub 94 and/or the cylindrical housing 44—such as adhesive bonding, friction fit, clamping and the like. In another embodiment, sleeve 99 is loosely placed over needle 91 and hub 94. A loose fitting or vented sleeve may be preferred (as compared to a sleeve that is stretched over the hub) in that it is presently believed to be less susceptible to oxidation during sterilization by electron beam or gamma sterilization. In the illustrated embodiment sleeve 99 is held in place by radially extending wall 64.

When a vial is inserted into housing 44, the end or septum of the vial forces the needle through the proximal end of the sheath 99 and into the vial. As the vial continues to be inserted, the sheath is forced distally to a collapsed configuration. When the vial is withdrawn, the resilient sheath 99 preferably resumes its position over the needle although such may not be required in sampling apparatus intended for one-time use only.

With a receiver assembly of the type described above, the technician can easily open and close the open proximal end of the holder assembly, as necessary. For example, once a sample has been collected (in the collection tube), the technician can, with a simple flick of his finger against the cap 70, close the housing 44. With another flick of the thumb or finger, the technician can open the housing to allow for insertion of the next tube. Thus, it will be appreciated that the easy manipulation of cap 70 provided by the present invention allows for a rapid, fluid and substantially uninterrupted sampling motion, while protecting the technician from accidental contact with the needle between sample draws, and from contact with blood residing in the holder interior. The holder assembly can later be reopened and utilized as a secure receptacle for a used venipuncture needle/needle protector, as described above. Fast and uninterrupted withdrawal is important because blood collected near the point of withdrawal from the donor or patient may not contain anticoagulant and it is important to be able to collect the sample before coagulation begins.

Figure 2A:
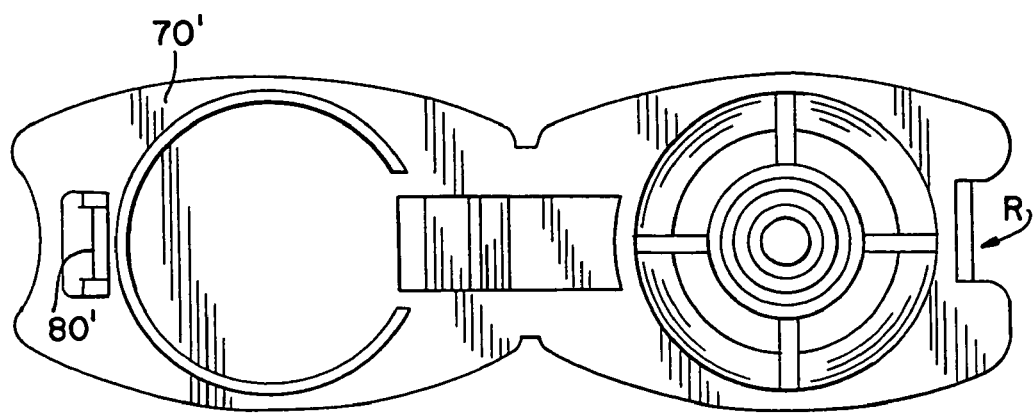
FIG. 2A is a top view of a sample tube receiver or holder with a modified cover design.

FIGS. 2A and 5A show alternative and preferred configurations of the cover or cap 70', needle subassembly 50' and housing 44'. As shown in FIG. 2A, the upper flange 51' of the housing 44' has a recessed edge area R. The cover 70' is sized to extend over and beyond the recessed edge area when in the closed position, with the latch 80' engaged to the flange at the recessed edge. The edge of the cover overlying the recess R is slightly concave. This provides a visible indicator to the user that the user's thumb or finger can be placed in this location to raise the cover.

FIGS. 5A and 5B show an alternative and preferred housing and needle assembly arrangement. The housing 44' is comparable to the housing 44 of FIG. 5 except that instead of a continuous internal rib 58, there are 4 spaced-apart rib arc segments 58', each of which extends a short distance around the inside of interior 56'. A small, generally rectangular opening or window W (formed by the molding apparatus) extends through interior wall immediately above each rib segment 58'. The windows allow the molding apparatus to better form the rib segments without deformation of the material when the mold opens.

The needle subassembly 50' in this embodiment is similar to that described earlier except that it has two radial flanges or rings 98'. Referring to FIG. 5B, upper ring 98', as seen in FIG. 5B, fits in snap engagement between the rib segments 58' and internal shoulder or ledge 59'. To prevent the escape of any blood that may leak from the inside of housing 44' through the windows W, the lower ring 98' is engaged in a fluid-tight interference fit against the surface of the interior wall 56'.

An alternative arrangement employing the present invention is shown in FIG. 6, which depicts a fluid circuit assembly in form of a blood processing set, like that shown in FIG. 1, with the exception of the sampling sub-unit. As shown in FIG. 6, fluid circuit assembly is a blood processing set principally intended for manual collection and processing of whole blood from a donor or other source. The blood processing set 10 shown there includes a needle 12, tubing 14 and 15 for conveying whole blood to a blood receiving container 16 and additional containers 20 and 24 connected, via tubing, to collection container 16, for receiving blood components after a separation process has been carried out. To provide for sampling of the whole blood received from the donor or other source, a sampling sub-unit 102 is provided as an integral part of the fluid circuit assembly. The sampling sub-unit 102 includes a sample-receiving container 104 and a sample tube receiver or holder 106. The container receives whole blood through tubing 110 which is attached to the blood inlet line 14 at junction 108.

The sampling sub-unit and alternative embodiments thereof are shown in FIGS. 7-11. Turning to FIG. 7, the sampling apparatus of the present invention, as illustrated in this embodiment, has advantages with respect to both handling and packaging. As seen in FIGS. 7-11, the sample-receiving container is preferably, but not exclusively, a flexible container in the form of a pouch formed by peripherally sealing together two facing flexible plastic sheets 112 and 114. The sheets, which may be of polyvinylchloride or other suitable material, either with or without plasticizer, that can withstand gamma or E-beam irradiation sterilization or autoclave sterilization, are peripherally sealed together along a peripheral edge 116 to define a generally closed internal chamber for receiving blood or other biological fluid through tubing 108. The container 104 may be of any suitable shape, but in the preferred embodiment, the container walls are shaped to direct the incoming blood (or other fluid if used in a non-blood collection fluid circuit) to a selected location in the interior chamber. In the embodiment shown in FIG. 7, the container is adapted for holding in a generally vertical position, as shown in FIG. 7, and fluid is directed into the lowermost region of the container by the inclined peripheral edges in the lower portion of the container. For purposes of reference and description in discussing its vertical position, the container is shown as having an imaginary vertical axis X.

To assist and accommodate the vertical disposition of the container 104, inlet tubing 108, as illustrated in FIG. 7, extends through the peripheral edge 116 in a direction which is at an acute angle A with respect to the imaginary vertical axis of the container.

To remove samples from the container, the sampling sub-unit 102 includes the sample tube holder or receiver 106 of the present invention, which is carried by a wall of the container and preferably directly attached to a wall of the container. The sample tube receiver or holder 106 is essentially identical to that previously described in FIGS. 2-5, and includes a generally cylindrical housing 44 with proximal and distal ends 46 and 48, and having a piercing member such as a needle 99 mounted therewithin for cooperation with a sample collection container or vial 100.

Figure 11:
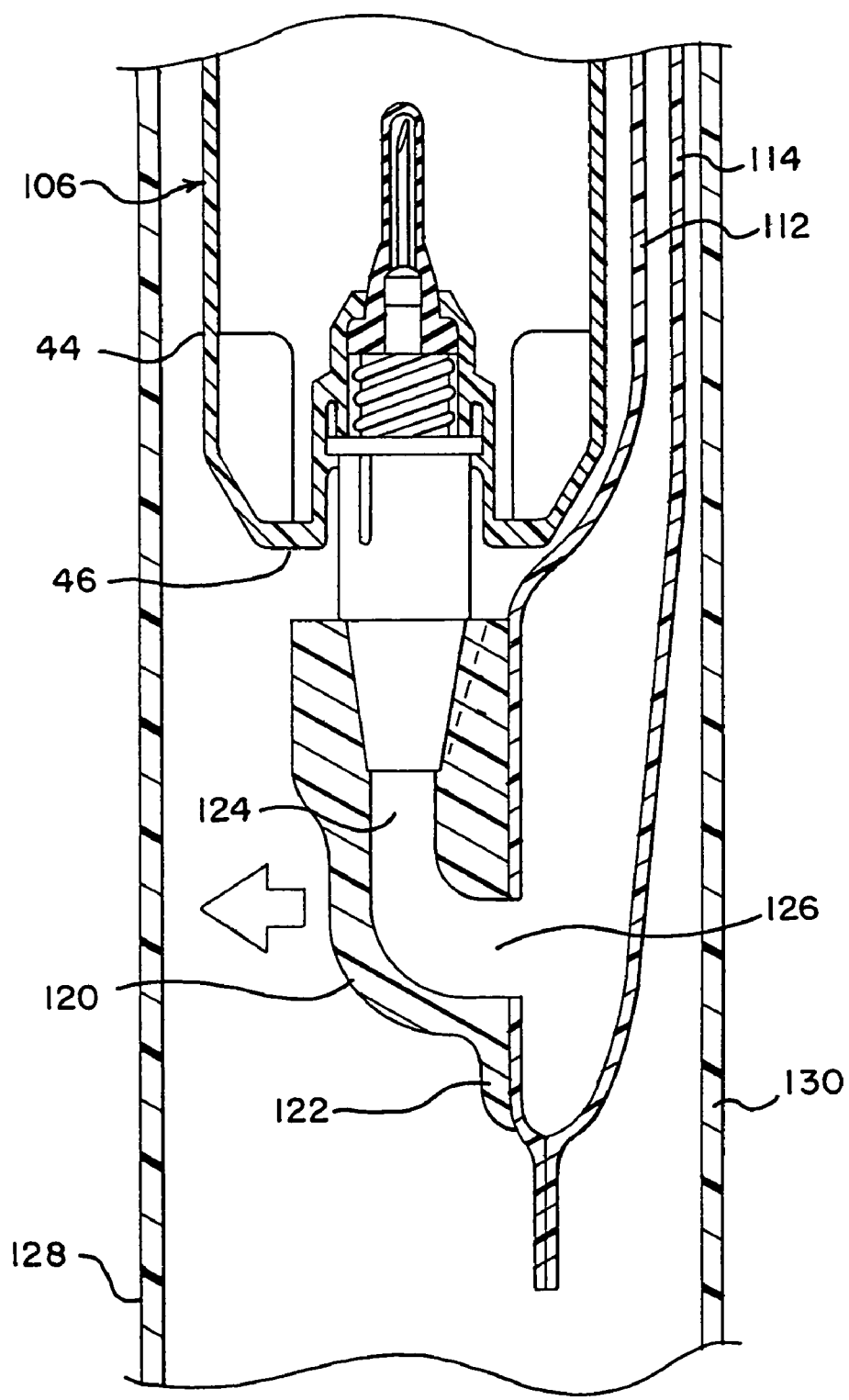
FIG. 11 is a vertical cross-section view of sampling apparatus taken along line 11-11 of FIG. 7 and illustrating the sampling apparatus within an outer package.

In the embodiment shown in FIG. 7, the distal end member 46 of the receiver assembly is attached, such as by ultrasonic welding, bonding or the like to a mounting member 120 that has a peripheral flange 122 for attachment to the flexible plastic sheet of the container. As best seen in FIG. 11, the mounting member 120 includes an interior passageway 124 that allows the sample tube receiver to communicate directly with a sample exit opening 126 located in the wall of the container. The exit opening 126 from the container is preferably located in the area where fluid collects and where is fluid is directed to collect by the walls of the container. In the embodiment shown in FIGS. 7 and 11, this is lowermost region of the container when the container is in the vertical disposition. To direct the blood to the lowermost region, the lower peripheral edges of the container, as seen in FIG. 7, are inclined to channel or funnel the fluid into the lowermost region. This arrangement better assures that substantially the entire sample collected within the container may be withdrawn if desired and has other advantages as well.

Figure 11A:
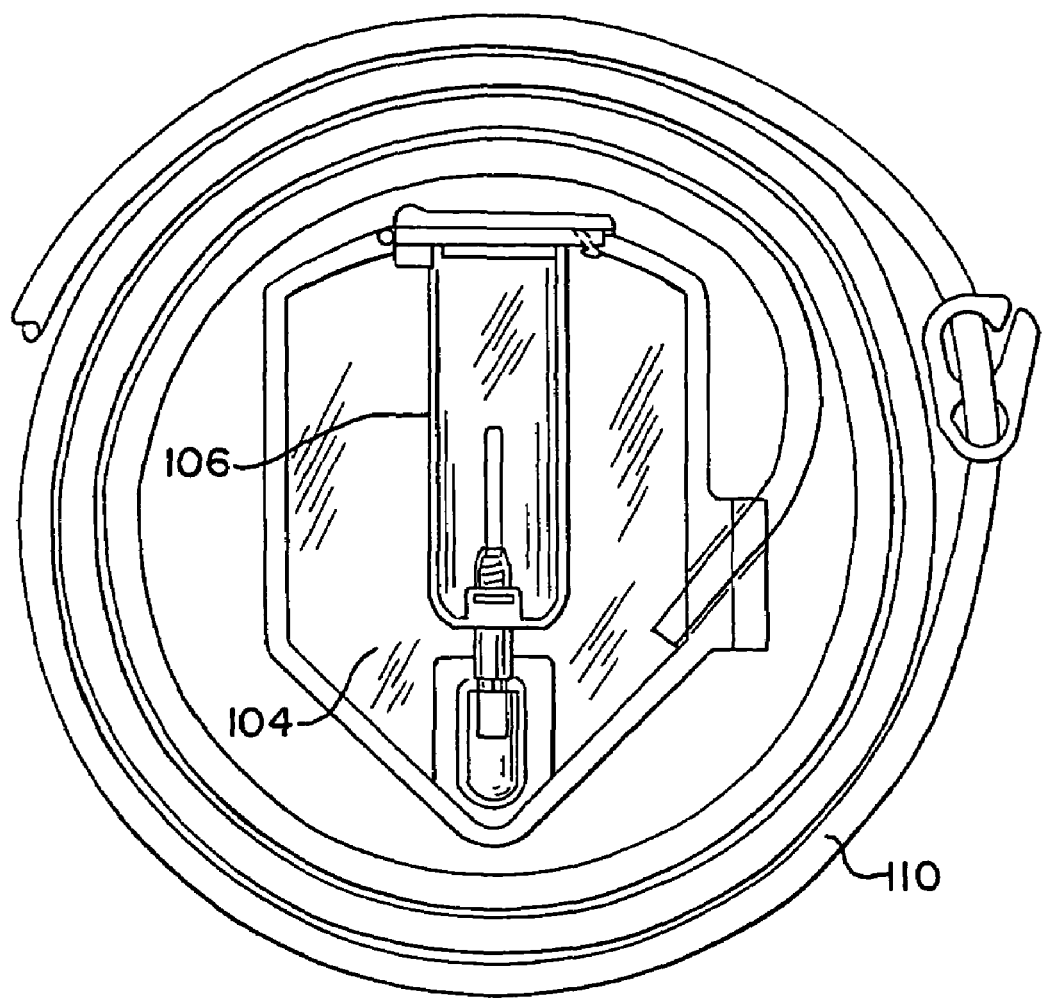
FIG. 11A is a plan view of the sampling apparatus of 7, showing the inlet tubing coiled around the container and receiver to provide a convenient and low profile packaging arrangement.

The sampling apparatus shown in FIG. 7 has the additional benefit of a compact, lay-flat configuration for packaging. As can be seen in at least FIGS. 7, 8 and 9, the sample tube holder or receiver 106 does not extend substantially beyond the peripheral edge of the container to which it is mounted, and substantially overlies the container. In other words, the receiver 106 is entirely or substantially within the "footprint" of the container. This aspect of the combined container and receiver cooperates with the angular direction of the tubing 108 to provide a convenient lay-flat configuration of the container and sample tube receiver, with the inlet tubing 108 coiled around it. For example, as seen in FIG. 11, the sample tube receiver and container provide a low profile packaging arrangement between upper and lower walls 128 and 130 of an outer package, and the coiled tubing fits easily with the low profile package, as illustrated in FIG. 11A.

Additional embodiments of the present invention, with differing configurations of the sample receiving container are shown in FIGS. 8-10. As shown in FIG. 8, the sample receiving container 132 is shaped similarly to that of FIG. 7, with the exception that the container includes a laterally extending region 134 at which the inlet tube 136 is attached in a generally vertical direction. Thus, the interior chamber of the container also includes, in part, a laterally extending region, into which the inlet tube 136 communicates. The sample tube receiver or holder 106 employed in FIG. 8 is essentially identical to that shown in FIG. 7, and is attached, by a mounting member 120, to a wall of the container so that it communicates with the interior chamber in the lowermost region of the container where the blood is directed.

Another embodiment of the sampling apparatus of the present invention is shown in FIG. 9. The sample container 138 of FIG. 9 is likewise made by peripherally sealing together a pair of flexible plastic sheets. In this embodiment as in the other embodiments discussed, the container could have one or more rigid walls, and be made of injection molded plastic, if it were so desired, without departing from broader aspects of the present invention.

The container 138 in FIG. 9 has a generally large central region 139 and a pair of opposed lateral regions 141 into which fluid flow tubing 140 and 142 communicate. In this embodiment, for example, tubing 140 could connect the container directly to the blood flow inlet line, and tubing 142 could be used for withdrawing blood from the container so that the sampling apparatus is not at the end of a fluid communication line, but is in-line in a fluid flow passageway that leads to another part of the fluid circuit.

Also intended for holding in a vertical disposition, the container 138 in FIG. 9 has a generally arcuate or upwardly concave lower peripheral edge, so that blood is directed into the lowermost region. The container wall includes an exit opening in the lowermost region to permit blood flow from the container to a sample tube located in the receiver 106. The receiver is mounted, via mounting member 120, in the same manner as described above with respect to FIGS. 7 and 11.

FIG. 10 shows another sampling apparatus embodying certain aspects of the present invention, which is identical to FIG. 9, except that the sample tube receiver is mounted in one of the laterally offset extending regions of the container, and the container does not have an outlet tube.

Figure 12:
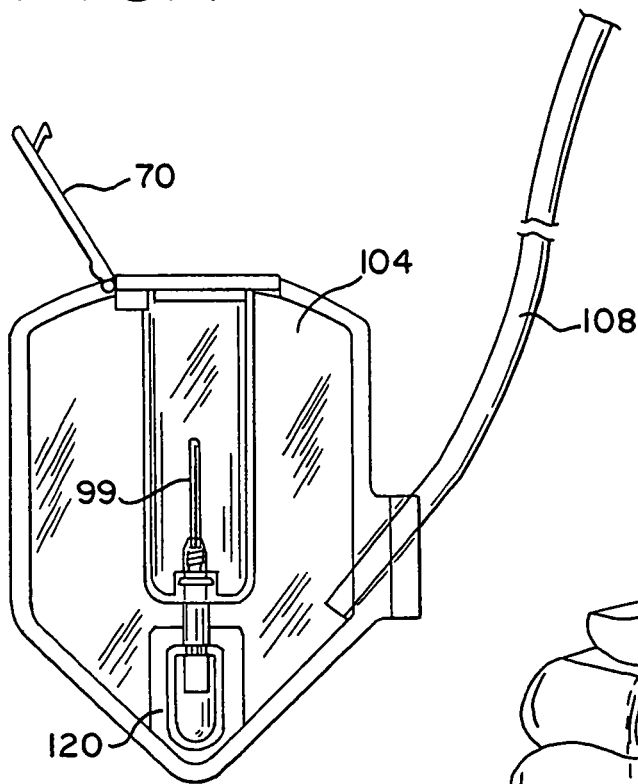
FIG. 12 is a plan view of the sampling apparatus of FIG. 7 with the receiver cover in the open position to receive a sample tube.
Figure 13:
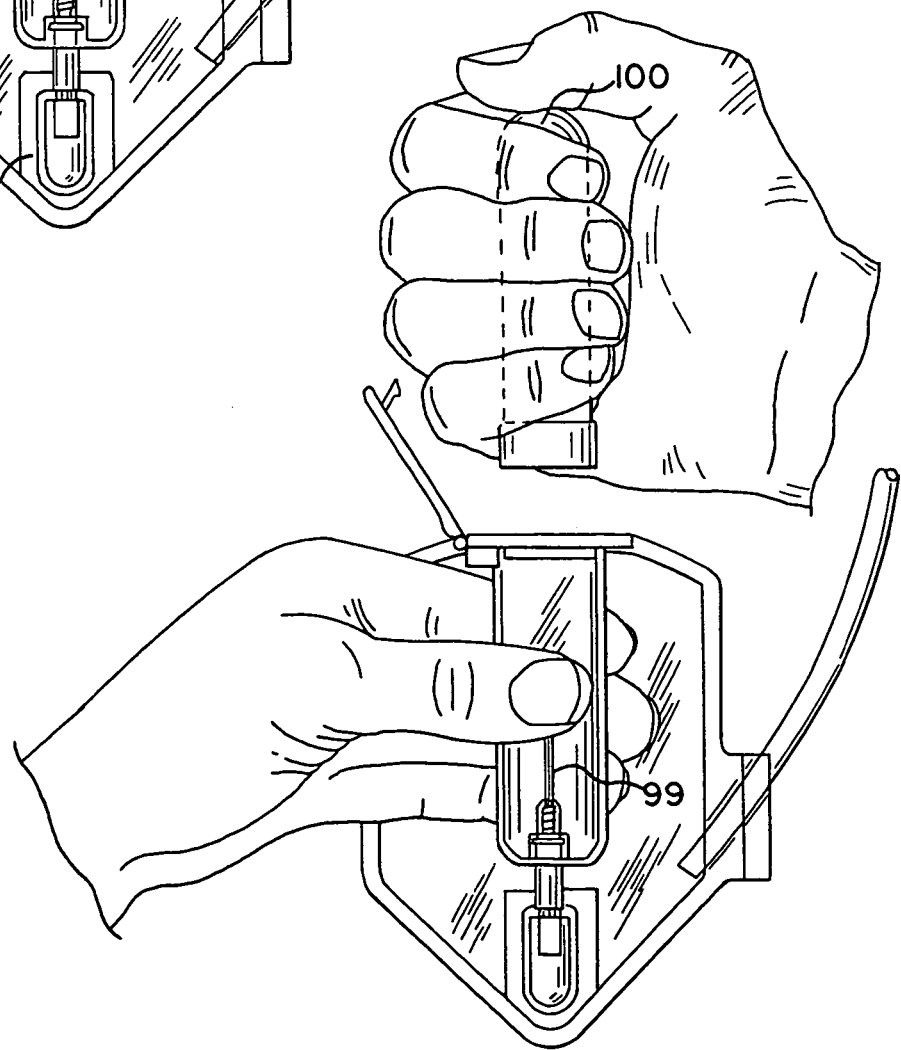
FIG. 13 is a plan view of showing insertion of a sample tube, such as a Vacutainer™ vacuum sample tube, into the receiver of FIG. 12.

FIGS. 12-13 show how the apparatus of the present invention may be employed in taking a sample from a fluid circuit assembly. Having collected a fluid sample through tubing 108 into the container 104, the container and receiver are held in a generally vertical position, with the proximal end of the receiver facing upwardly, and the cover or cap of the container is opened. As explained earlier, the living hinge arrangement moves the cap to an open position with a simple flick of the thumb to raise the cap. The blood collection vial or tube 100 is then inserted downwardly into the receiver, as shown in FIG. 13. The blood collection tube includes a septum of latex or other suitable material at the bottom of the tube that is pierced by the needle 99 located within the cylindrical housing of the receiver. The interior of the blood collection tube typically is a vacuum, which tends to draw contents from the sample outlet in the lowermost region of the container upwardly through the mounting member and needle and into the collection tube. This procedure, which requires minimal manipulation of the container and blood sample and employs a vertical insertion of the sample tube, has the further advantage of reducing hemolysis of the blood or blood component. Repeated samples can be taken simultaneously or periodically as usage requires. When the sample has been taken, the cap on the tube receiver is closed to protect the interior needle from accidental engagement by the user.

As described earlier, in addition to possible stand-alone applications, the present invention may be used in both manual and automated fluid circuit assemblies. FIGS. 1 and 6 illustrate typical manual fluid circuit assemblies for blood and blood component collection. FIG. 14 illustrates a fluid circuit assembly specifically intended for automated collection and processing and employing the sample apparatus of the present invention. Except for the sample apparatus of the present invention, the fluid circuit assembly and automated collection device shown in FIG. 14 are as described in detail in U.S. Pat. No. 6,325,775, which is incorporated by reference herein.

The fluid circuit, generally at 144, shown in FIG. 14 is intended for use with a portable, suitcase-size processing device 146. Without repeating all of the disclosure set forth in the above-identified patent, which is incorporated by reference, the disposable fluid circuit assembly shown in FIG. 14 includes a fluid circuit control module 148 which is adapted for mounting onto the device 146, and which has associated controllers for controlling the direction and flow through the fluid circuit. The fluid circuit assembly may also include a separation device, generally at 150, through which anticoagulated whole blood flows for separation into one or more blood components, such as red cells, platelets or plasma. The fluid circuit assembly may also include miscellaneous containers 152 for receiving blood or blood components or for containing anitcoagulant, saline, or other liquids required during the blood processing.

In accordance with the present invention, blood sampling apparatus or sub-unit 102 is attached to the fluid circuit assembly at a Y-site or V-site junction 154 in the line leading from the donor access needle, preferably before anticoagulant is added to the whole blood at junction 155, although it may be attached at any other location in the fluid circuit where there is a need or desire to sample the fluid at that location. In all other respects, the sampling apparatus 102 is identical to that described earlier in connection with FIGS. 7 and 11-13.

Turning now to a description of the needle 99 employed in the sample receiver, it should first be noted that the needle may be used to repeatedly puncture the rubber or latex septum of a sample tube, and it is desirable that the needle not unduly damage the septum or generate particulate matter.

Figure 15:
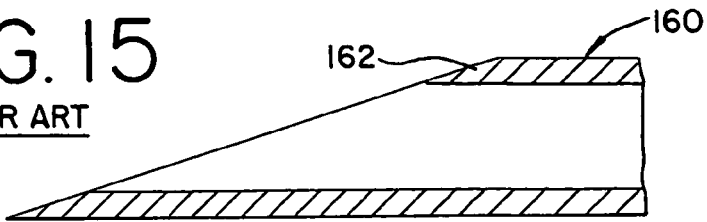
FIGS. 15-16 are cross-sectional and top views, respectively, of the piercing end of a prior art needle.
Figure 16:
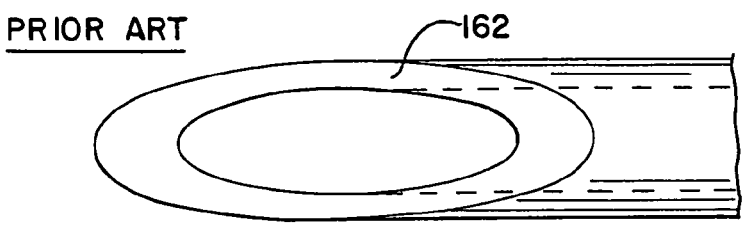

FIGS. 15-19 show prior needle tip designs that have been employed in various medical applications. FIGS. 15-16 show the sharpened end of a stainless steel needle 160, employing a straight bevel facet to form the needle tip. FIG. 15 is a cross-sectional view of such a needle, and shows a straight or plain beveled surface 162. FIG. 16 shows the same needle and the elliptical facet surface 162 from a top view.

Figure 17:
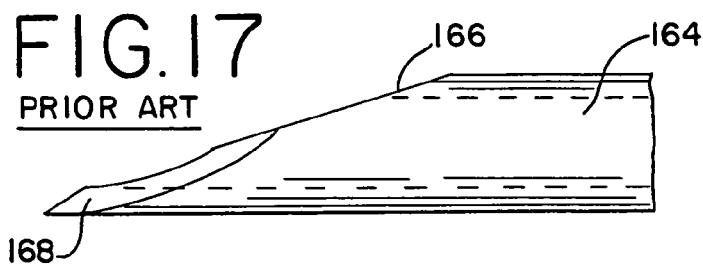
FIGS. 17-19 are side, top and bottom views, respectively, of the piercing end of another prior art needle.
Figure 18:
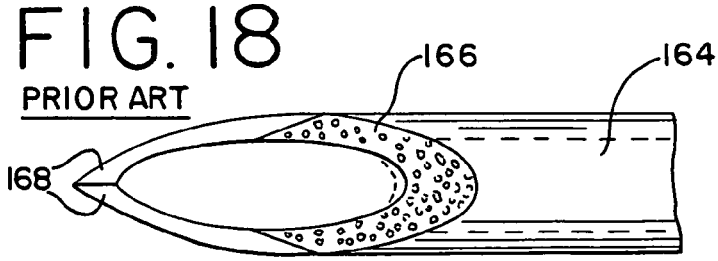
Figure 19:
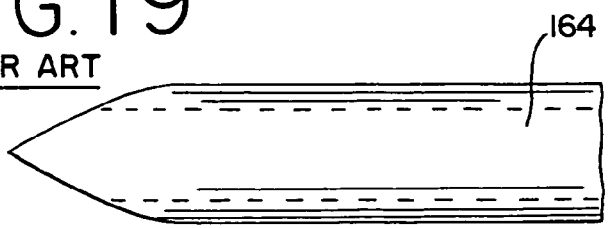

FIGS. 17-19 illustrate another prior needle 164. The sharpened tip of needle 164 has a flat or straight primary bevel grind surface 166 in a proximal region of the needle tip, and outwardly angled (or downwardly diverging) secondary bevel facets 168 leading from the flat bevel to the distal most end of the needle tip. The primary bevel is subjected to microsandblasting, a technique known in the field, which erodes the edges of the primary bevel to make the heel of the needle opening more rounded.

FIGS. 20-23 show the tip configuration of a needle 170 as preferably used in the fluid sampling apparatus of the present invention. The needle tip there includes a generally flat primary needle grind to generate facet 172 in a proximal region of the needle tip. A pair of inwardly angled (or downwardly converging) secondary side bevel grind surfaces or facets 174 are next formed sequentially at the distal most end of the needle tip. These secondary facets may be formed by rotating the needle shaft in one direction for a selected angle greater than 90° and less than 180°, grinding one secondary facet and then rotating the needle back to the start position and then in the other direction at the same angular displacement, where the other secondary facet is ground. The two secondary facets preferably extend not more than about 30% of the length of the primary bevel. The intersection of the internal surface of the hollow needle with the proximal portion of the primary bevel (the heel) can be a very sharp edge or blade that is responsible for coring of the septum or other material pierced by the needle. To reduce the potential for coring, the proximal portion of the primary bevel, at least in the area of the heel, is preferably microsandblasted to smooth the sharp edges and reduce the potential for coring. The side bevel facets 174 converge at the tip to form the distal most tip 176 of the needle at an interior location spaced a distance D from the side surface of the needle shaft.

Tests of the needle 170 show substantially improved results relative to septum destruction or particle generation. FIG. 26 shows a typical collection tube septum 180 repeatedly punctured or pierced six times with the needle 170. The puncture area is visible, but limited and confined to generally one location. FIG. 25 shows such a septum repeatedly pierced six times with the prior art needle of FIGS. 15-16. This needle tends to enter the septum at different locations with each puncture, and the tearing and destruction of the septum is more severe and is not localized.

FIG. 24 shows an alternative needle 180 which may also provide for improved septum piercing in which the needle tip is generally plain and closed, except for a lateral rectangular aperture 182 formed in the side of the needle wall for fluid communication after the septum has been pierced by the closed point of the needle shaft.

Although the present invention has been described in terms of the illustrated embodiments, the intended scope of the invention is as set forth in the appended claims and the illustrated embodiments in this description are intended as an illustration and not intended as a limitation to the subject matter set forth in the claims.

What is claimed is:

1. Sampling apparatus comprising
    a sample container including at least one wall defining a fluid-receiving interior chamber in which the container is adapted to be held in a selected position for withdrawing a fluid sample, in which position the container has a generally vertical axis, the apparatus further comprising a fluid inlet for receiving fluid into the chamber and flexible tubing communicating with the fluid inlet, the tubing being disposed at an acute angle to the vertical axis and
    a sample device receiver carried by the container wall and in fluid communication with the chamber, the receiver being adapted to receive a sampling device for withdrawing a fluid sample from the chamber.

2. The apparatus of claim 1 in which the tubing extends in a coil configuration around the container to provide a compact configuration for packaging.

3. Sampling apparatus comprising:
    a sample container including at least one wall defining a fluid-receiving interior chamber and wherein the container has an outer peripheral edge, wherein said container is adapted to be held in a selected position for withdrawing a fluid sample, said container including walls shaped to form a lowermost point in the interior chamber and to direct fluid in the interior chamber to the lowest point in the chamber when the container is in the selected position, the container further including a fluid inlet for receiving fluid into the chamber; and
    a sample tube receiver carried by the container wall wherein the receiver is situated such that the receiver is located substantially within the outer peripheral edge and no part of the receiver extends substantially beyond the peripheral edge, the receiver being adapted to removably receive therethrough a sampling tube for withdrawing a fluid sample from the chamber, the receiver communicating with the interior chamber in the vicinity of the lowermost point so that substantially all of the fluid within the interior chamber may be withdrawn.

4. The apparatus of claim 3 in which the sample tube receiver is disposed to receive a sampling tube in a vertical direction when the container is in the selected position.

5. Sampling apparatus comprising
    a sample container comprising facing flexible plastic sheets peripherally sealed together to define an interior chamber, wherein the container has an outer peripheral edge, the container further including a fluid inlet for receiving fluid into the chamber, the container being adapted for holding in a generally vertical disposition and the peripheral edges is inclined to direct fluid into a lowermost region of the chamber when the container is in the vertical disposition, and a sample tube receiver carried by the container wall wherein the receiver is situated such that the receiver is located substantially within the outer peripheral edge and no part of the receiver extends substantially beyond the peripheral edge, the receiver being adapted to removably receive therethrough a sampling tube for withdrawing a fluid sample from the chamber.

6. Sampling apparatus comprising a sample container including at least one wall defining a fluid-receiving interior chamber and wherein the container has an outer peripheral edge, the container further including a fluid inlet for receiving fluid into the chamber and a sample tube receiver carried by the container wall wherein the receiver is situated such that the receiver is located substantially within the outer peripheral edge and no part of the receiver extends substantially beyond the peripheral edge, the receiver being adapted to removably receive therethrough a sampling tube for withdrawing a fluid sample from the chamber, the receiver further comprising a needle assembly including a piercing end and a non-piercing end;

a generally cylindrical housing including a distal end engageable with the needle assembly, a proximal end adapted to receive a blood collection tube, and a sidewall extending between the proximal and distal ends; and a cover movably associated with the proximal end of the cylindrical body and movable between a closed position covering the proximal end and an open position opening the proximal end.

7. The apparatus of claim 6, wherein the distal end of the housing further comprises a through-bore defined by an interior wall.

8. The apparatus of claim 7 in which the housing and needle assembly have interlocking surfaces for fixedly holding the needle assembly in the through bore.

9. The apparatus of claim 8 wherein the needle assembly includes radially extending rib; and the interior wall of the through bore defines a slot for receiving and securing said radial rib of the needle assembly.

10. The apparatus of claim 8, wherein the slot in the interior wall of the through bore is defined between a first inwardly extending radial ledge and a second inwardly extending radial ledge axially spaced from the first inwardly extending ledge.

11. The apparatus of claim 6, further comprising a sleeve disposed over the piercing end of the needle assembly.

12. The apparatus of claim 11 in which the interior wall of the through bore further includes an inwardly projecting member engageable with the sleeve.

13. The apparatus of claim 6, wherein said cover is attached to said housing by a hinge.

14. The apparatus of claim 13, further comprising a closure member that has a first end attached to the cover and a second end attached to the housing, the closure member being disposed to hold the cover in either the open or closed position and to move the cover preferentially from an intermediate position to the open or closed position.

15. A disposable fluid circuit assembly for processing, storing, separating or treating a biological fluid such as blood or blood components, an inlet for receiving a biological fluid into the fluid circuit assembly;

one or more flow paths for conducting the biological fluid or components thereof between selected locations within the fluid circuit;

a sample container including at least one wall defining a fluid-receiving interior chamber and wherein the container has an outer peripheral edge, the container further including a fluid inlet for receiving biological fluid or component into the chamber; and a sample device receiver carried by the container wall and in fluid communication with the chamber wherein the receiver is situated such that the receiver is located substantially within the outer peripheral edge and no part of the receiver extends substantially beyond the peripheral edge, the receiver being adapted to receive a sampling device for withdrawing a fluid sample from the chamber.

16. The fluid circuit assembly of claim 15 in which the container is adapted to collect fluid at a selected area in the interior chamber and the sample device receiver communicates with the chamber at the selected area.

17. The fluid circuit assembly of claim 15 in which the tubing extends in a coil configuration around the container to provide a compact configuration for packaging.

18. The fluid circuit assembly of claim 15 in which the container comprises facing flexible plastic sheets peripherally sealed together to define the interior chamber, the receiver overlying one of the sheets and communicating through such sheet with the interior chamber.

19. The fluid circuit assembly of claim 15 in which the container comprises walls shaped to direct fluid to the selected area in the interior chamber.

20. The fluid circuit assembly of claim 15 in which the container is adapted for holding in a generally vertical disposition and the container includes walls shaped to direct fluid in the interior chamber to the lowest point in the chamber when the container is in the vertical disposition, the receiver communicating with the interior chamber in the vicinity of the lowest point so that substantially all of the fluid within the interior chamber may be withdrawn.

21. The fluid circuit assembly of claim 20 in which the sample device receiver is disposed to receive a sampling device in a vertical direction when the container is in the vertical disposition.

22. The fluid circuit assembly of claim 15 in which the container comprises facing flexible plastic sheets peripherally sealed together to define the interior chamber, the container being adapted for holding in a generally vertical disposition and the peripheral edges are inclined to direct fluid into a lowermost region of the chamber when the container is in the vertical disposition.

23. The fluid circuit assembly of claim 22 in which the receiver communicates with the lowermost region of the chamber.

24. The fluid circuit assembly of claim 15 in which the receiver comprises a tubular member, one end of the tubular member being open or openable for receiving a sample tube and the other end communicating with the chamber, the tubular member including a hollow piercing member located in the interior of the tubular member and in fluid communication with the interior chamber and disposed to enter a sample tube inserted into the tubular member.

25. The fluid circuit assembly of claim 24 in which the sample container is adapted to be held in a vertical orientation and the tubular member is disposed to extend in a generally vertical direction, with the one end facing upwardly when the sample container is in a vertical orientation so as to allow a sample tube to be inserted vertically downwardly into the tubular member.

26. The fluid circuit assembly of claim 15 in which the receiver comprises:

a needle assembly including a piercing end and a non-piercing end;

a generally cylindrical housing including a distal end engageable with the needle assembly, a proximal end adapted to receive a blood collection tube, and a sidewall extending between the proximal and distal ends; and a cover movably associated with the proximal end of the cylindrical body and movable between a closed position covering the proximal end and an open position opening the proximal end.

27. The fluid circuit assembly of claim 26, wherein the distal end of the housing further comprises a through bore defined by an interior wall.

28. The fluid circuit assembly of claim 27 wherein the needle assembly and housing have interlocking surfaces for fixedly positioning the needle assembly in the through bore.

29. The fluid circuit assembly of claim 28, wherein a slot is defined in the interior wall of the through bore and the needle assembly includes an annular rib for interfitting in the slot.

30. The fluid circuit assembly of claim 27, wherein the needle assembly further includes a sleeve disposed over the piercing end of the needle assembly.

31. The fluid circuit assembly of claim 26, wherein said cover is attached to said housing by a hinge.

32. The fluid circuit assembly of claim 31, further comprising a closure member with a first end attached to the cover and a second end attached to the housing, the closure member being disposed to hold the cover in either the open or close position and to move the cover preferentially from an intermediate position to the open or closed position.

33. The disposable fluid circuit assembly of claim 15 wherein said sample container comprises a pair of flexible facing plastic sheets peripherally sealed together along a peripheral edge to define an interior chamber and adapted for holding in a generally vertical disposition, a blood component inlet tube communicating between the chamber and one or more flow paths or selected locations within the fluid circuit, the peripheral edge being inclined to direct blood component in the chamber to a lowermost region of the chamber when in the vertical position and a blood component sample exit opening located in one of the sheets in the lowermost region.

34. The fluid circuit assembly of claim 33 wherein the sample container includes a main pouch region and at least one laterally offset pouch region and the blood component inlet tube is attached to the pouch at the laterally offset region.

35. The fluid circuit assembly of claim 33 further includes a blood component removal tube communicating with the chamber.

36. The fluid circuit assembly of claim 35 wherein the sample container includes a main pouch area and opposed laterally offset pouch regions, the blood component inlet tube being attached to the pouch at one of the laterally offset regions and the blood component removal tube being attached at the other laterally offset region.

37. A disposable fluid circuit assembly for processing, storing, separating or treating a biological fluid such as blood or blood components, an inlet for receiving a biological fluid into the fluid circuit assembly;

one or more flow paths for conducting the biological fluid or components thereof between selected locations within the fluid circuit;

a sample container including at least one wall defining a fluid-receiving interior chamber and including a fluid inlet for receiving biological fluid or component into the chamber in which the container has a generally vertical axis and in which the assembly further comprises flexible tubing communicating with the fluid inlet, the tubing being disposed at an acute angle to the vertical axis; and a sample device receiver carried by the container wall and in fluid communication with the chamber, the receiver being adapted to receive a sampling device for withdrawing a fluid sample from the chamber.

38. The fluid circuit assembly of claim 37 wherein the inlet is adapted for withdrawing whole blood from a human and the fluid circuit comprises a flow path for conducting the whole blood or a component thereof to a desired location within the fluid circuit, the fluid inlet to the interior chamber communicating with the blood or blood component flow path for receiving a sample of the blood or blood component into the chamber.

39. A disposable fluid circuit assembly for processing, storing, separating or treating a biological fluid such as blood or blood components, an inlet for receiving a biological fluid into the fluid circuit assembly;

one or more flow paths for conducting the biological fluid or components thereof between selected locations within the fluid circuit;

a sample container including at least one wall defining a fluid-receiving interior chamber and including a fluid inlet for receiving biological fluid or component into the chamber and in which the container includes a main chamber region and at least one laterally offset chamber region and the fluid inlet to the chamber is located in the laterally offset region and;

a sample device receiver carried by the container wall and in fluid communication with the chamber, the receiver being adapted to receive a sampling device for withdrawing a fluid sample from the chamber.

40. The fluid circuit assembly of claim 39 in which the container includes opposed laterally offset chamber regions.

41. The fluid circuit assembly of claim 40 further comprising a fluid outlet located in laterally offset chamber region.

42. A method for taking a sample of biological fluid comprising:

providing a sampling apparatus comprising a sample container including at least one wall defining a fluid-receiving interior chamber and including a fluid inlet for receiving fluid into the chamber;

a sample device receiver carried by the container wall and in fluid communication with the chamber, the receiver being adapted to receive a sampling device for withdrawing a fluid sample from the chamber wherein the sample receiver further comprises a tubular member with a proximal end and a distal end and a cover removably covering the proximal end and the method includes opening the cover;

holding the sample device receiver and sample containers such that the receiver is disposed to receive the sample device into operative position for sample withdrawal in a generally vertical direction;

inserting the sample device into the receiver in a generally vertically downward direction, the sample receiver communicating with a lowermost region of the sample container as held so as to withdraw a sample generally vertically into the sample device; and withdrawing the sample device after a sample is withdrawn and closing the cover over the proximal end.

43. Sampling apparatus comprising a sample container including at least one wall defining a fluid-receiving interior chamber and including a fluid inlet for receiving fluid into the chamber and wherein said sample container comprises a pair of flexible facing plastic sheets peripherally sealed together along a peripheral edge to define an interior chamber, the container being adapted for holding in a generally vertical disposition, a blood component inlet tube communicating with the chamber, the peripheral edge being inclined to direct blood component in the chamber to a lowermost region of the chamber when in the vertical position and a blood component sample exit opening located in one of the sheets in the lowermost region, and a sample tube receiver carried by the container wall and in fluid communication with the chamber, the receiver being adapted to removably receive therethrough a sampling tube for withdrawing a fluid sample from the chamber.

44. The sampling apparatus of claim 43 wherein the sample container includes a main pouch region and at least one laterally offset pouch region and the blood component inlet tube is attached to the pouch at the laterally offset region.

45. The sampling apparatus of claim 43 further includes a blood component removal tube communicating with the chamber.

46. The sampling apparatus of claim 45 wherein the sample container includes a main pouch area and opposed laterally offset pouch regions, the blood component inlet tube being attached to the pouch at one of the laterally offset regions and the blood component removal tube being attached at the other laterally offset region.

* * * * *